(12) United States Patent
Nyirucz et al.

(10) Patent No.: US 10,195,376 B2
(45) Date of Patent: Feb. 5, 2019

(54) DEVICE AND METHOD FOR ADMINISTRATION OF COMPOSITIONS TO THE EUSTACHIAN TUBE

(71) Applicants: Alex Nyirucz, Bellerose, NY (US); Richard Lee Strauss, Freeport, NY (US)

(72) Inventors: Alex Nyirucz, Bellerose, NY (US); Richard Lee Strauss, Freeport, NY (US)

( * ) Notice: Subject to any disclaimer, the term of this patent is extended or adjusted under 35 U.S.C. 154(b) by 90 days.

(21) Appl. No.: 15/530,366

(22) Filed: Jan. 3, 2017

(65) Prior Publication Data

US 2018/0185593 A1    Jul. 5, 2018

(51) Int. Cl.
*A61M 15/08*    (2006.01)
*A61M 11/02*    (2006.01)
*A61M 15/00*    (2006.01)

(52) U.S. Cl.
CPC .......... *A61M 15/085* (2014.02); *A61M 11/02* (2013.01); *A61M 15/0045* (2013.01)

(58) Field of Classification Search
CPC ................ A61M 15/085; A61M 11/02; A61M 15/0045; A61M 31/00; A61M 11/007
USPC ............. 604/26, 514, 11, 19, 506, 187, 275, 604/94.01, 274; 128/898, 200.23, 200.14, 128/200.18, 200.19, 200.21, 206.11
See application file for complete search history.

(56) References Cited

U.S. PATENT DOCUMENTS

2011/0152838 A1\* 6/2011 Xia ........................ A61M 11/06
604/514

\* cited by examiner

*Primary Examiner* — Manuel Mendez
(74) *Attorney, Agent, or Firm* — Richard L. Strauss, Esq.

(57) ABSTRACT

A nasal administration device is disclosed which enables delivery of a well collimated stream of medication through the nasal orifice of a human being to the pharyngeal orifice of the eustachian tube. The device utilizes alignment tabs to properly position the collimated stream utilizing facial landmarks and an alignment arrow to confirm such alignment. Certain preferred embodiments of the disclosed device include adjustable alignment tabs enabling more precise alignment for a range of facial profiles.

28 Claims, 27 Drawing Sheets

DEVICE AND METHOD FOR ADMINISTRATION OF COMPOSITIONS TO THE EUSTACHIAN TUBE

FIELD OF INVENTION

The disclosed invention is most closely related to the technical field of nasal administration devices and methods utilized to deliver pharmaceutical agents to a human patient via the nasal orifice.

BACKGROUND OF THE ART

Otitis media is a pathological condition common to humans, and most common to children. During episodes of otitis media, fluid accumulates in the middle ear or, as it is also known, the tympanic cavity.

Acute otitis media is a condition in which fluid accumulation in the middle ear is accompanied by signs or symptoms of ear infection (including both viral and bacterial etiologies). Such pathology may exhibit a bulging eardrum accompanied by pain or, in some instances, perforation of the tympanic membrane. Such perforations may also be accompanied by drainage of purulent material. In contrast, otitis media with effusion, also known as serous otitis media, is typified by fluid accumulation within the tympanic cavity without signs of infection.

Both acute otitis media and otitis media with effusion may cause substantial pain as pressure increases, positively or negatively, within the confines of the tympanic chamber. Antibiotics, steroids, and antibiotics in combination with steroids have been utilized to treat otitis media. Antihistamine/decongestants have also been utilized in the treatment of otitis media with effusion.

The anatomical features of the middle ear define what can be described as a sealed chamber. On its lateral border, the middle ear is effectively isolated from the external auditory meatus (in the absence of a punctured ear drum), by the intact tympanic membrane. Medially, the middle ear is effectively sealed from the inner ear by a bony wall. The posterior wall of the tympanic cavity communicates with a large, but effectively sealed mastoid antrum. Only the anterior wall of the middle ear contains a passageway for effective communication outside of the tympanic cavity. There, a natural pathway provided by the auditory or, as it is also known, the eustachian tube, provides communication with the nasopharynx. The eustachian tube is normally closed, sealing the middle ear/mastoid chamber, and opens at intervals to equalize pressure between the nasopharynx and middle ear.

During episodes of acute otitis media, the painful increased middle ear pressure may naturally resolve through a resultant perforation of, and drainage through, the tympanic membrane. However, such perforation is unusual and the increased fluid pressure associated with otitis media with effusion does not resolve via this mechanism. In fact, for those patients suffering otitis media for prolonged periods of time, (three months or more) and especially for those evidencing significant associated hearing loss, myringotomy with the placement of a tympanostomy is indicated as a means of equalizing middle ear pressure and in order to restore normal hearing. Unfortunately, during episodes of otitis media with effusion (OME), a time when the natural pathway and pressure relief functions of the eustachian tube would be most useful, the increase pressure required to open the lumen (as described in more detail above and below), effectively eliminates this means of relieving middle ear pressurization. Reduced patency of the eustachian tube is believed to be one of the primary causes of OME in pediatric patients. In fact, it is known that OME elevates eustachian tube opening pressure independent of other pathological conditions effecting this conduit. U.S. Pat. No. 6,616,913 (Sep. 9, 2003) ("THE '913 patent") discloses a method of increasing and enhancing mammalian eustachian tube lumen patency and pressure equalization performance by administering an aerosolized mixture of lipid crystals comprised of a mixture of one or more lipids surfactants and one or more spreading agents selected from the group consisting of cholesteryl esters, phospholipids, carbohydrates, and proteins, in powder form, and one or more fluorocarbon propellants through a mammalian nasal orifice. Upon administration, the propellant(s) are evaporated from the mixture and the lipid crystals are deposited and, through the action of the spreading agent, reach the pharyngeal terminus of the eustachian tube. As the lipid crystals come into contact with luminal surfaces of the eustachian tube, an amorphous spread film is formed thereupon substantially decreasing the opening pressure of the lumen. Pathologic conditions such as otitis media, are effectively treated by decreasing eustachian tube opening pressure as a pathway for release of the pressurized contents of the middle ear is provided via the proper physiologic opening and depressurization function of the eustachian tube lumen so as to quickly relieve the pain caused by such pressure while also promoting resolution of the subject infection. The '913 patent also disclosed incorporation of a therapeutically active agent effective in the treatment of otitis media added to the mixture of lipid crystals. Upon administration of said aerosol mixture, the amorphous spread film formed thereby carries said therapeutically active agent through the eustachian tube to the tissues of the middle ear so as to effectively treat the underlying pathologic condition. (See U.S. Pat. No. 6,616,913, abstract)

The '913 patent teaches the use of a metered dose nasal administration device to deliver the subject mixture of lipid crystals, both with and without a therapeutically active agent, to the eustachian tube via the nasopharyngeal orifice thereof. As stated in the '913 patent, a mixture of one or more lipids and one or more spreading agents selected from the group consisting of cholesteryl esters, phospholipids, carbohydrates, and proteins, all in powder form, and one or more fluorocarbon propellants is first prepared. The lipids and the spreading agents are advantageously selected to be insoluble in the propellants. The lipids utilized in practicing the method of the present invention are present in an amount of about 80 to 99.5 percent by weight and the spreading agents are present in an amount of about 0.5 to about 20 percent by weight, both based upon the total weight of the mixture. Combination of the one or more lipids, one or more spreading agents and one or more fluorocarbon propellants results in the formation of lipid crystals and described in more detail, below. A metered dose of the mixture of lipid crystals is then administered, via an external nasal orifice into a mammal upon which the present method is practiced.

The '913 patent discloses application of the subject mixture of lipid crystals via a metered dose nasal administration device so as to more closely control dose administration. However, without means of delivering a focused stream of lipid crystals through the nasal orifice to the eustachian tube and a means of targeting the pharyngeal orifice of the auditory tube with such a focused stream, a significant portion of the mixture is ineffectively applied to other mucosal surfaces. Administration of the aerosolized lipid crystals through the nasal orifice utilizing administration devices of the prior art devoid of a means of targeting the eustachian tube and/or focusing the stream of crystals administered thereby results in, at best, an indiscriminate, shotgun-like deposition of said crystals upon the mucosal surfaces of the sinus passages and sinus airways. The mucosal surfaces of these airways and sinuses demonstrate an air/liquid interface formed by the secretion of muco- and muco-serous secretions thereupon.

Upon deposition of the lipid crystals upon these mucosal surfaces, said crystals form a uniform and amorphous spread film and effectively reduce the surface tension thereupon. (See U.S. Pat. No. 6,616,913, col 6, lines 40-43). Although it would be expected that such an indiscriminate application would allow the surfactant/spreading agent to eventually spread to and flow into the eustachian tube's pharyngeal orifice, the above-described delivery devoid of any targeting means would not be optimal or capable of efficient, rapid and selective application.

Ordinarily, and, as shown in many commercials, advertisements, drug inserts and other media, patients, and those applying medications to patients utilizing nasal administration devices, utilize such devices in such a way as to direct the spray provided thereby in a relative upward direction towards the patient's ethmoid with no particular or provided targeting guidance. This is the natural and expected mode of use of such devices in the vast majority of prior art nasal administration and inhalation techniques as such devices were intended to dispense compounds to the tissues of the nose, the sinuses or, in other instances, to a large portion of the respiratory system via inhalation—without any intended discrete area of application—. For such applications, utilizing a nasal administration device in the usual upward direction, or, for that matter, with no particular direction whatsoever, was perfectly acceptable. Equally acceptable for application of medications not intended for a discrete application to a structure—such as the eustachian tube orifice—, was a shotgun-like dispersion of medicine provided by the devices of the prior art. Simply put, in the prior art, the medications carried by such devices were never intended for specific and or discrete areas. However, in regard to the lipid crystals discussed above, or, for that matter, any other compositions, compounds or medications—specifically intended for application to the eustachian tube or middle ear via nasal administration, such incorrect or random application is expected to reduce the speed, efficiency and optimum effect otherwise provided by precise targeting of the nasopharyngeal orifice of the auditory tube.

More specifically, at the present time, there is no known negative effect resulting from application of a portion of the above-discussed lipid crystals (disclosed in the '913 patent) to the mucosa lining the sinuses and upper respiratory surfaces rather than limiting application to the mucosa directly adjacent to the nasopharyngeal opening of the eustachian tube. However, such applications, in the form of a mis-directed and unfocused medication delivery, would be expected to require a greater amount of medication and a greater amount of time to take effect as much of the composition would be applied to areas quite distant from the eustachian tube's pharyngeal orifice. Certainly, a large portion of a haphazardly applied unfocused stream of such medication would result in a greater amount so dispensed never reaching the eustachian tube. Thus, it would be highly advantageous if a nasal administration device could be designed, arranged and configured to deliver the aforementioned crystals, or, any mixture intended for delivery to the eustachian tube and/or middle ear—via the eustachian tube—, in a substantially focused (collimated) and targeted manner to the mucosal lining of the nasopharynx adjacent the pharyngeal orifice of the eustachian tube. It would be still further advantageous if a method and device could be disclosed to administer a well collimated stream of said lipid crystals from a device which included a means of providing accurate positioning of the device so that a collimated stream delivered thereby would be directed to the region of the nasopharynx in close proximity to the eustachian tube orifice.

SUMMARY OF THE INVENTION

Now in accordance with the present invention, a nasal administration device, especially designed, configured and adapted for the accurate and focused delivery of a composition to the lumen of the eustachian tube of a human is provided. The term "composition" as utilized throughout this description and within the claims refers to any composition(s), mixture(s) and/or medicaments which can be utilized for the treatment of any condition and/or, pathology involving the eustachian tube, middle ear, or the enhancement of any function of the eustachian tube or middle ear which necessitates application of such materials to or through the eustachian tube of a patient and the middle ear.

The device of the present invention comprises an administration housing and a delivery nozzle, or, as it may be referred to, with equal and the same meaning, a collimation nozzle. For this purpose, it may be utilized in conjunction with a canister bottle contained within the administration housing. This canister is the source of the compound(s), compositions and/or medications to be delivered by the device of the present invention. The present invention also contemplates using the claimed device for the administration of compound(s), compositions and/or medications contained in other metered and non-metered dose canisters so long as such canisters are capable of providing, upon actuation, a stream of such compounds(s), compositions and/or medications capable of flowing through and being delivered by the device, as described, below. For this purpose, pressurized canisters capable of delivering contents contained therein without a metered dose chamber and valve, as well as canisters which delivery contents via a pump mechanism may equally be utilized with the present invention. The canisters utilized may also be integrated as a continuous part of the administration housing. It is also contemplated that the device of the present invention may be utilized with medication contained within "blister packs", the contents of which are propelled through the device by a liquid propellant, compressed gas, or pump actuation utilizing atmospheric air.

In a preferred embodiment of the present invention, a metered dose canister, for example, may be utilized as the source of the composition contained within and administered by the device as a collimated stream directed towards the pharyngeal orifice of the eustachian tube. More specifically, the term "directed towards the pharyngeal orifice of the eustachian tube" or "directing the collimated stream towards the pharyngeal orifice of the eustachian tube" as utilized throughout this specification and claims means directing the collimated stream to the lateral wall of the nasopharynx at the level of the inferior nasal concha—the region of the nasopharynx where the orifice is located—. It is preferred that the collimated stream emanating from the device upon activation is directed to a position within a 15 mm radius of the pharyngeal orifice of the eustachian tube orifice. However, it is further preferred that the administration device is configured to deliver a collimated stream with a 10 mm radius of the nasopharyngeal orifice of the auditory tube. A metered dose canister, a device well known to the art, is comprised of a tubular shaped canister bottle having a proximal terminus and a distal terminus. A longitudinal axis runs centrally through a main chamber, located at the proximal portion of the canister and a constricted portion of the canister chamber located adjacent to the distal portion of the canister. The canister bottle is open at the distal terminus only. The main chamber of the canister is located adjacent to the closed proximal terminus of the canister and is adjacent to the constricted portion of the canister located towards the distal open proximal terminus of the bottle. The constricted portion includes a central bore in fluid communication with the central bore of the main chamber of the canister bottle. The constricted portion of the canister is especially designed, shaped and configured to accept and matingly engage a metering valve assembly which is well known to the art.

While there are many designs of the metering valve canister, and the valve body incorporated therein, they basically operate following the same principles. The metering canister is filled with a compound to be delivered to a patient. Prior to actuation, a first conduit located within the metering valve assembly is open and forms a pathway between the main chamber of the canister bottle and a metering chamber formed within the metering valve. The metering chamber and first conduit contain a predetermined amount of compound. The metering chamber acts to control (meter) the amount of canister contents released upon each actuation. As the metered dose device is actuated, ordinarily by depressing the valve stem, discussed below—the first conduit closes and there is no longer a fluid connection between the metering chamber and the main chamber. At this point in operation, another conduit connects the metering chamber to the atmosphere outside of the canister. The conduit is formed in a distal portion of the valve stem connecting the metering chamber to, in instances wherein it is a metered dose canister bottle utilized with the present invention, an administration nozzle.

The pressurized formulation that had been measured and contained within the metering chamber is thus released rapidly into the valve stem, which, together with the actuator seating, forms an expansion chamber in which the propellant begins to boil. The canister is ordinarily utilized in the inverted position, with the valve located at the proximal end of the canister, below the container so that the valve will refill under gravity. Some valves are surrounded by a retaining cup that contains the next few doses of vessel contents. Other valve designs are well known to the art. However, in practicing the present invention, the specific type canister bottle, use or non use of a metering valve, type of valve selected, means of canister material delivery (pressurized, propellant, pump, etc), as well as use of an integrated canister or a separate canister inserted into the housing is not limiting. For example, virtually any embodiment of a metered dose canister of the prior art can may successfully and advantageously utilized in practicing the present invention as can non-metered dose pressurized canisters (or those utilizing a suitable propellant) or non-propellant containing canisters which utilize a pump. Also, the administration housing may be configured to contain the composition to be delivered without use of a separate container.

In the first preferred embodiment of the present invention, a nasal administration device is disclosed which includes a delivery nozzle especially shaped and configured to form and direct a highly collimated and concentrated stream of a compound(s) and/or composition(s) to be delivered, via the nasal orifice, to the pharyngeal orifice of the eustachian tube. For this reason, the term "delivery nozzle" as utilized throughout this specification and within the claims, has the same and equal meaning as the term "collimation nozzle". The collimation nozzle is comprised of a hollow tube defining a central bore having a selected diameter. Two termini, a proximal and distal termini, are located at opposite ends of the hollow tube. The distal termini as well as the distal portion of the nozzle is advantageously shaped and configured for placement within the nostril of a human patient while the proximal termini as well as the proximal portion of the nozzle is shaped and configured for secure mating, and fluid communication with a delivery port, described below. The distance between the two termini defines the length of the collimation nozzle. The central bore of the nozzle demonstrates a selected, constant, continuous and uniform diameter running the entire length of the collimation nozzle so as to enhance collimation and reduce lateral dispersion. The bore is in fluid communication with openings located at opposite ends/termini of the nozzle. The openings located at the proximal and distal termini of the delivery nozzle demonstrate diameters equal to one another and also equal to that of the central bore so as to produce a collimated stream. The surfaces lining the central bore and openings are configured to be smooth and devoid of any irregularities that might otherwise interfere with the production of the collimated stream.

In practicing the first preferred embodiment of the present invention, the collimation nozzle is especially selected to demonstrate a diameter that reduces the amount of lateral dispersion of a specific selected compound, mixture or medicament to be administered through the nozzle for delivery to the pharyngeal orifice of the eustachian tube. For example, a collimation nozzle can be designed, shaped and configured to deliver the mixture of lipid crystals of the '913 patent, discussed above, upon activation of the actuator and release of said mixture to the eustachian tube with a minimum amount of scattering. The resultant collimated stream enables accurate and efficient delivery of the mixture to the intended eustachian tube orifice target. The collimated nozzle of the present invention avoids indiscriminate scattering, fanning or wide dispersion of compound(s), compositions and/or medications delivered by the device so as to avoid literally spraying such materials over most of the internal surfaces of the nasal cavity, nasal pharynx and sinuses. Such an application would naturally be expected to minimize the amount of material directed towards the pharyngeal orifice of the eustachian tube, require greater amounts of composition sprayed to provide a desired amount to the eustachian tube and delay delivery to the targeted tissues of the eustachian tube and middle ear.

Put simply, the diameter of the collimation nozzle is selected to provide effective collimation or, in other words, focus of the stream of materials delivered by the device of the present invention which, as discussed below, is capable of directing such a focused stream to that region of the pharynx wherein the orifice of the eustachian tube is located. The term "collimation" as utilized herein, refers to the focusing of the stream of liquid, powder or combinations thereof emanating from the collimation nozzle so as to minimize indiscriminate dispersion of said stream. In this way, the compounds streaming from the nozzle may be directed some distance from the nozzle without substantial spread or loss of concentration.

For this same purpose, the diameter of the central bore of actuator collimation nozzle as well as the proximal and distal terminus thereof, is selected to be uniform—and without areas of constriction, enlargement or other diameter irregularity—so as to reduce lateral dispersion of compounds such as, for example, a mixture of lipid crystals, powders, liquids and mixtures thereof, released therethrough after activation of the nasal administration device providing such compounds.

Beyond forming the central bore of the delivery nozzle (as well as the openings at the distal and proximal termini thereof), so as to be uniform in diameter, specific diameter ranges for said nozzle and termini are advantageously selected, depending upon the specific content of the composition(s), materials and/or medications actually delivered by the device of the present invention, are selected to further optimize collimation. The optimal diameter range for each such material may be obtained via test actuations, as discussed below. For example, in regards to the aerosolized mixture of lipid crystals discussed above, it has been discovered that it is preferred to form the central bore of the delivery nozzle as well as the openings formed at both termini thereof, with a uniform and preferred diameter of from about 0.6 mm to about 0.9 mm for this purpose.

The administration housing of the present invention is comprised of a canister containment section and a delivery nozzle section. The canister containment section of the housing is an elongated hollow structure having a front wall, rear wall and two side walls. The canister containment section also includes openings located at the superior and inferior termini thereof. A large central bore, having a longitudinal axis, runs the longitudinal length of the canister housing and is continuous with the openings at the superior and inferior termini thereof. The large central bore is designed and configured to demonstrate a shape and size which enables placement and secure retention therein of a selected canister containing compound(s), compositions and/or medications to be delivered. In the first preferred embodiment, the canister utilized with the device can be selected to be, for example, a metered dose canister. For this purpose, the superior terminus of the canister containment section is especially shaped and configured to define an opening of sufficient size and shape so as to enable passage therethrough of a metered dose canister of a given diameter. The inferior terminus of the housing is shaped and configured to define a shape and opening which enables mating engagement thereof with the superior terminus of the delivery nozzle section. The length of the administration housing is advantageously selected to enable a small portion of the distal portion of the metered dose canister to extend beyond the housing thereby providing easy access to depressing same against the metered dose canister housing to achieve device activation (as discussed in detail, below.) As mentioned above, the present invention also contemplates embodiments wherein the administration housing itself is utilized to contain the composition to be delivered.

Extending from the front wall of canister containment section—although affixed, in some embodiments to the side walls thereof—a canister containment section alignment tab is provided. The tab is advantageously mounted so that it extends, for example, from the front wall of the canister containment section of the housing forward, away from the front wall at a 90 degree angle. The tab may also be mounted upon the side walls of the canister containment section, the front wall, or combinations thereof so long as it extends forward relative to the front wall of the canister section. In the first alternate preferred embodiment of the present invention, discussed below, the alignment tab can be an adjustable alignment tab that is adjustably mounted to the canister housing section in, for example, a slideable configuration. The slideable feature of the adjustable alignment tab enables the tab to extend away from the front wall of the canister section as well as retract back towards the canister containment section. The present invention also includes embodiments wherein the adjustable canister containment alignment tab also provides for movement along the longitudinal axis of the canister containment section so as to conform to a wider range of facial anatomies (profiles and dimensions). However, the first preferred embodiment utilizes a non-adjustable, or, as they may also be referred, fixed alignment tab(s). The size, length and configuration of both the fixed, and adjustable canister containment section alignment tabs are designed and configured so as to enable stable placement of the device against the a patient's nose. For this purpose, it is highly desirable to utilize the bridge of a patient's nose for such placement, although other regions of the nose, adjacent to this region, may be utilized. For this purpose, a distal contoured terminus and portion of said tabs are especially shaped and configured for stable contact of the tab against the a patient's nose—and in preferred embodiments against the bridge portion of a patient's nose—, although such a configuration is not limiting. Other embodiments of the present invention may utilize such tabs for placement upon other regions of the nose such as, for example, that region of the nose both below and above the bridge portion. Such contact, while simultaneously placing the delivery nozzle of the device within a patients nostril, provides great stability when utilizing the device while—as discussed in great detail below—simultaneously aligning the longitudinal axis of the delivery nozzle with the eustachian tube's pharyngeal orifice in regard to elevation. In addition, in examples of the first preferred embodiment having both a canister section alignment tab as well as a delivery nozzle alignment tab, even more stability is provided. The purpose of incorporating the fixed, non-adjustable canister containment section alignment tabs as well as the fixed delivery nozzle section alignment tab in certain preferred embodiments of the present invention, beyond providing the aforementioned stability, is to properly orient the device so as to direct a collimated stream emanating from the collimation nozzle during activation in a correct elevational orientation—towards the pharyngeal orifice of the eustachian tube —. The length, size and position of fixed alignment tabs are selected to achieve the aforementioned purpose for a majority of child and adult facial configurations, shapes and sizes.

As discussed in more detail, below, alternate embodiments of the present invention incorporate the above-mentioned adjustable canister containment section alignment tabs and/or adjustable delivery nozzle section alignment tabs so as to provide greater accuracy in the application of the device to a wider range of patient facial shapes and sizes. Such greater application and accuracy is provided by the ability of the tabs to be extended away from as well as retracted towards the canister administration housing in order to finely tune angulation of the longitudinal axis of the delivery nozzle toward the eustachian tube orifice. Determination that the device is so properly positioned is provided by reference to the elevation alignment line/arrow formed within or upon the side walls delivery nozzle section of the housing—discussed in great detail, below—. However, the present invention also contemplates embodiments not incorporating the delivery section arrow. In such embodiments, the canister alignment tab and delivery nozzle, when placed in an administration position, as described below, enables the collimated stream emanating from the device to be directed towards the pharyngeal opening of the eustachian tube. In still further embodiments, the canister containment alignment tab may be adjustable as to superior and inferior position along the longitudinal axis of the housing so as to accommodate faces of greater length. In the alternative, the administration housing itself may be provided in different sizes to provide varying distances between the canister containment section tab and delivery nozzle section tabs so as to accommodate different patient facial sizes and contours.

In preferred embodiments of the present invention, a midline alignment line is formed upon the midline of the rear wall of the canister containment housing in such a position as to be aligned with the longitudinal axis of the housing. As explained in more detail, below, this midline alignment line is advantageously utilized to enable a user (or administrator of the device), to position the device during activation, parallel to the midline of a patient face. Such positioning causes the collimated spray emanating from the nozzle to be directed directly into the plane of the face—without medial or lateral deviation—. This alignment is intended to direct the spray in such a manner as to increase accuracy in targeting the pharyngeal opening of the eustachian tube which is located in general alignment with a pathway running back from each nostril into the nasopharynx rather than deviating substantially either medially or laterally away from the eustachian tube.

The delivery nozzle section of the administration housing of the preferred embodiment includes a superior terminus, an inferior terminus, a front wall, back wall, two side walls and a central bore. The superior terminus of the nozzle delivery section is open and is especially shaped and configured so as to enable secure mating thereof with the inferior terminus of the canister section. Furthermore, located within the central bore of the nozzle delivery section and adjacent to the superior terminus thereof, a docking port is formed and is advantageously shaped and configured for secure insertion of and matting with, for example, the constricted portion of the metered dose canister bottle as well as the valve stem extending from the metered dose valve. The docking port may also be configured for the receipt, mating and fluid connection of any other canister type or shape utilized with the device. The nozzle docking port is designed and configured to provide fluid connection, by means of a conduit formed within the docking port, with a delivery nozzle port formed upon the front wall of the delivery nozzle section. The delivery port, in turn, is especially shaped and configured to matingly and securely engage and form fluid communication with a delivery (collimation) nozzle as well as the central bore formed therewithin.

The delivery nozzle includes a central bore having a longitudinal axis as well as proximal and distal termini demonstrating uniform and constant diameter. When the device is configured for use with the above-described mixture of aerosolized lipid crystals, the central bore as well as the openings of the termini of the delivery nozzle are selected to demonstrate a diameter range—as discussed above and below—which optimizes the collimation of a stream of administered compound, for optimal delivery of such to the pharyngeal terminus of the eustachian tube. Other diameters are selected to achieve optimal collimation dependent upon the specific material to be delivered by the device. The actuator collimation nozzle is advantageously mounted upon a delivery nozzle port in such a manner as to orient the central bore thereof in a 90 degree relation with the longitudinal axis of the delivery section and cannister containment section housing. A delivery nozzle cap may also be optionally provided so as to keep foreign matter from entering into the distal end of the delivery nozzle when not in use. The delivery nozzle may extend at angles other than 90 degrees relative to the longitudinal axis of the delivery and cannister containment sections as long as the alignment tab(s) are shaped and configured to properly target the pharyngeal orifice of the eustachian tube with the collimated stream emanating therefrom when the device is placed in position as described above and below. In all embodiments, the elevation alignment arrow/line, discussed below, must be aligned with the longitudinal axis of the delivery nozzle and the collimated stream produced thereby.

A delivery section alignment tab is advantageously located and positioned upon the front surface of the delivery section adjacent to the inferior terminus of the delivery nozzle section. This alignment tab extends, for example, at an approximate 90 degree angle to the longitudinal axis of the canister containment and delivery nozzle sections of the administration housing at a point just below the delivery nozzle port and adjacent to the inferior terminus of the delivery section. The delivery section alignment tab includes a contoured portion at the distal terminus thereof which is especially contoured in a concave manner to enable close adaptation and contact with a patient—just above the upper lip and below the nostril into which the delivery nozzle is placed—and, most advantageously, upon a philtral column just below the nostril in which the nozzle is placed.

As described below, preferred embodiments of the present invention include elevation alignment lines, or, as they also may be referred to, equally and with the same meaning herein, elevation alignment arrows, formed within or upon the side walls of the delivery section of the housing. The elevation alignment lines/arrows are oriented and positioned to be parallel to and in alignment with both the longitudinal axis of the delivery nozzle and the stream of collimated composition(s), compound(s) and/or medication(s) emanating therefrom. The purpose of the elevation alignment line/arrow is to enable a patient, or a person administering medication utilizing the device, to position the device in such a manner so as to increase accuracy in directing the collimated stream towards the pharyngeal opening of the eustachian tube. However, the present invention includes embodiments without an elevation alignment line/arrow which utilize the positioning provided by placement of the canister section alignment tab against a patient's nose—including the bridge of a patient's nose—, in conjunction with placement of the delivery nozzle within the patient's nostril, and in some embodiments, placement of the delivery canister alignment tab against a philtral column, to properly align and direct the collimated stream emanating from the device to the pharyngeal orifice of the eustachian tube.

In practicing the method of the present invention, a canister, such as a metered dose canister, filled with a medicament to be delivered to the eustachian tube is docked within the preferred administration housing of the present invention so that the valve stem extending therefrom as well as the constricted portion of the bottle (in canisters demonstrating same) are in mating engagement with the docking port and in fluid communication with the docking port conduit, the central bore of the nozzle port and the central bore of the delivery nozzle. The delivery nozzle is then placed in an external nasal orifice of a patient with the canister containment section alignment tab positioned against the patient's nose—most advantageously, in the region of the bridge of a patient's nose—and, in embodiments including same, the delivery section alignment tab placed above the upper lip in the region of the philantrum (as discussed above and below). This placement ordinarily results in a delivery device attaining a position that orients the longitudinal axis of the delivery nozzle, and the collimated stream provided thereby, towards the pharyngeal opening of the eustachian tube. In regard to preferred embodiments of the present invention including elevation alignment line/arrow formed in or upon the side walls of the delivery nozzle section of the housing, such positioning also results in said line/arrow pointing to the tragus of the patient's ear on the same side of her face as the nostril entered. This line/arrow orientation further assures that the collimation nozzle—having a longitudinal axis in parallel alignment with said elevation line/arrow—, as well as the collimated stream that arises therefrom is in alignment—relative to elevation angle—with an imaginary line running from the naris (nostril) to the tragus, a naris/tragus elevation alignment line. The naris/tragus elevation alignment line is an imaginary (or reference) line connecting those two anatomical landmarks, the tragus of the ear and the naris of the nose. This pathway defines an elevation line connecting the naris with the pharyngeal orifice of the eustachian tube. The naris/tragus alignment line moves in a lateral direction as it runs from each of these external facial landmarks (nostril and tragus) to the other. This lateral displacement is not followed in use of the method of the present invention as the actuator nozzle is placed, by means of the alignment tabs and the midline alignment mark on the back wall of the housing, in a manner that directs the collimated spray directly into the plane of the face towards the normal position of the eustachian tube orifice without lateral displacement. If, for example, and in opposition to the present method, one were to direct the collimated stream, laterally, along the lateral displacement of the nasal/tragus elevation line, such would cause the stream to collide with the lateral walls of the nasal meatus as well as other nasal structures. Directing the stream directly back, into the plane of the face, causes the stream to flow, virtually unimpeded, save for instances of deviated nasal septum, through to the nasopharynx where following the correct nasal/tragus elevation results in accurate targeting of the eustachian tube. However, positioning the device so that the alignment arrow points towards the tragus provides the proper and accurate elevational direction so as to direct the collimated spray towards the eustachian tube orifice target. Thus, beyond positioning the device so that the alignment arrow is directed towards the tragus, the longitudinal axis of the administration housing is kept in a parallel relationship—via, in certain preferred embodiments, the midline alignment mark—with the midline of the patient's face so as to avoid lateral or medial mis-alignment of the device.

As discussed in much greater detail below, in embodiments in which a metered dose or other propellant/pressurized canisters are utilized, depressing the distal end of the canister at the open (superior) terminus of the administration housing with the device oriented and positioned following the present method results in a release of compound through the collimation nozzle (as discussed above). The compound released forms a well collimated stream directed towards the pharyngeal opening of the eustachian tube with much improved accuracy—as opposed to random administration via devices of the prior art devoid of the stabilizing and positioning tabs of the present invention that properly and accurately direct medication to the intended target as well as the elevation and midline alignment marks thereof that further enable great accuracy in such target acquisition.

The first alternate embodiments of the present invention utilize adjustable canister containment and/or delivery nozzle section alignment tabs. In such embodiments wherein, for example, an adjustable canister containment section tab is provided, such tabs may be slidably mounted so as to extend away from and retract towards the canister containment section. Longitudinal adjustments of such tabs along the length of the canister section may also be provided. Other embodiments may include adjustable delivery nozzle alignment tabs providing the same extension and retraction. Such adjustments allows for accurate alignment and delivery of medications to the eustachian tube in a wide range of patients having differing facial profiles and dimensions. The first preferred embodiments of the present invention having at least one fixed, (non sliding canister) containment tab(s) provide increased delivery accuracy as compared to any device found in the prior art which are devoid of any such positioning and/or targeting means whatsoever. However, those embodiments of the present invention including adjustably mounted tabs provide greater ease in achieving and repeating such accurate application of medication in regard to a wider range of facial profiles, sizes and shapes due to the ability, as discussed below, to fine tune the orientation of the device and set it in a stable. configuration for repeatable and accurate targeting.

For many patients, use of the first preferred embodiment of the present invention incorporating a fixed (on non-adjustable) alignment tabs, will provide eustachian tube targeting for superior to the unfocused random application devices of the prior art. In utilizing such fixed configurations, upon proper placement of the respective canister containment and delivery section alignment tab(s) against the bridge region of the nose and philantrum area, accurate alignment is attained. The length and dimensions of the alignment tabs and delivery nozzles are especially shaped and configured for this purpose. Embodiments of the present invention with both a first (configured for placement upon bridge of nose) and second alignment tab (configured for placement above lip and below nose) are formed and dimensioned so that the length, contour and positioning of the tabs result in proper elevational alignment with the eustachian tube orifice. Such embodiments can, of course, be configured for different age and size ranges. Also, embodiments having only a first alignment tab (for placement against the bridge of the nose) are also configured so that after such placement, and entry of the nozzle into the patient's nostril, proper alignment is achieved. In the majority of instances, such correct placement can be checked by confirming, in those embodiments including a delivery section elevation alignment line/arrow—that such line/arrow to points to the tragus of the patient's ear and thus will deliver a collimated stream of medication following the same slope (elevation path) as the naris/tragus elevation alignment line. However, in instances of certain facial profile contours and dimensions, the alignment arrow may point below or above the patient's tragus when the device is so positioned against the bridge of the nose and within the patients' nostril. This indicates that, in this preliminary position, the collimated stream emanating from the device will be below or above the desired elevational alignment. In such instances, the first preferred embodiments of the present invention—without an adjustable (slideable) canister containment tab and/or delivery nozzle alignment tab require—manual repositioning of the device to attain alignment of the elevation alignment line with the tragus is expected to result in loss of stabilizing contact of at least one of the canister alignment or delivery alignment tabs with the patient's face. Also such manual adjustment of position must be checked, confirmed and repeated each time of application to assure the best and most properly directed application to the target eustachian tube nasopharyngeal aperture.

In the first alternate preferred embodiments of the present invention incorporating an adjustable canister section alignment tab, and, in certain preferred examples thereof, both an adjustable canister containment and delivery nozzle alignment tab, the adjustable tabs may be extended or retracted to a position whereby, when the contour portions of both tabs are placed upon the patient's nose, —most advantageously, against the bridge of the nose—and in the region of the philantrum, proper and repeatable alignment is achieved to optimize targeting of the eustachian tube. More specifically, in embodiments of the present invention utilizing adjustable tabs, such tabs are initially extended or retracted from a central neutral position until placement of the respective tabs against the root of the nose and the philtral column cause the elevation alignment arrow pointing (correctly) to the tragus. The adjustable tabs are especially designed, configured and adapted to provide sufficient resistance to movement so that they can reliably maintain a position set by an administrator so as to allow proper alignment to be set via the adjustable tabs one time only. Subsequent applications utilizing the pre-adjusted slideable tabs thus result in accurate, repeatable applications of medicine to the eustachian tube. In embodiments of the present invention including adjustable canister alignment tabs that provide for longitudinal movements along the length of the canister containment section, the canister alignment tab is adjusted until the tab may be placed upon the bridge of the nose while the delivery nozzle is inserted into the patient's nostril. In embodiments including a delivery nozzle section tab, that section tab is placed against the philtral column just below the nostril entered via the delivery nozzle.

In a second alternate embodiment of the present invention, a nasal administration device is disclosed which is especially configured and adapted for the delivery of medicaments through the nose to the pharyngeal orifice of the eustachian tube of an infant. This device may also be utilized for adolescents and adults. As in regard to the embodiments discussed above, the second alternate embodiment of the present invention is especially designed, configured and adapted for the accurate and focused nasal administration of compositions to the pharyngeal orifice of the eustachian tube. The second alternate embodiment of the present invention comprises a collimation nozzle and an administration housing.

If, for example, the second alternate embodiment of the present invention is utilized with a metered dose canister, such a canister is the same or similar to those described above and well known to the art. Likewise, the collimation nozzle utilized in the second alternate embodiment demonstrates the same form with a constant and uniform bore diameter and openings at the proximal and distal termini as discussed above. However, the administration housing utilized in the second alternate embodiment is unique in its design and configuration which is highly advantageous so as to properly and most efficiently deliver medications to an infant.

Due to the relatively diminutive size of an infant's head, face and the relative difference in facial profile and the degree of compliance/patient cooperation anticipated, it is highly advantageous to provide an administration housing that allows rapid and uncomplicated delivery with a minimum of required steps. This second alternate embodiment may also be appropriate for some adolescent and adult patients who, due to physical, emotional or mental condition, may present challenges to administration. For this reason, the second alternate embodiment of the present invention incorporates an administration housing comprised of a canister containment section and administration nozzle section devoid of the alignment tabs discussed above, but including an elevation alignment line/arrow that provides for rapid and correct orientation of the device for proper direction of a collimated medication stream towards the pharyngeal opening of the eustachian tube. The back portion of the canister containment section of the second alternate embodiment includes a midline alignment line formed upon or within said wall and which is in parallel alignment with the longitudinal axis of the canister containment section of the administration housing. As discussed below, this midline is utilized to assure that the device is oriented parallel to the midline of the infant's face and that the collimated stream emanating therefrom is administered directly into the facial plane of the patient's face without substantial lateral or medial deviation.

The administration housing of the second alternate embodiment is comprised of a canister containment section and a delivery nozzle section. The canister containment section of the housing is a simple, hollow tube especially shaped and configured to contain and securely retain a canister bottle such as, for example, metered dose canister. However, the second alternate embodiment may also be configured for use with non-metered dose canisters utilizing propellants and/or pump actuated canisters. In embodiments especially configured for a metered dose canister, the canister containment section includes an open superior terminus which enables passage therethrough of a metered dose canister and includes a front portion, back portion and two side portions. The distal terminus of the canister containment section is especially shaped and configured to mate with and securely engage the superior terminus of the administration nozzle section discussed below. The canister containment section demonstrates a length slightly less than the length of a canister bottle so as to enable a small portion of the distal end of, for example, a metered dose canister to extend beyond the canister containment section. This extension allows access to depress the distal end of the bottle for actuation of the valve which is thus biased against the docking port, discussed below—and release of pressurized compound(s), mixture(s) and/or medicaments from the device—. Such movement may alternately be utilized to actuate a pump actuated canister bottle. The canister containment section also includes two finger rests extending from the outer surface of the front and rear portions of the canister containment section adjacent the proximal terminus thereof located approximately opposite one another (in a 180 degree relation). The finger rests provide, as discussed below, a means of holding and easily manipulating the position of the device during use as well as finger holds to press against when depressing the canister bottle—with, for example, an additional finger—during operation of the device. As mentioned above and below, the back portion of canister containment section includes a midline alignment line.

The delivery nozzle section of the administration housing defines a short hollow cylinder having two side surfaces, a front surface and a back surface. The delivery nozzle section of the administration housing also demonstrates an open superior terminus especially shaped and configured to mate with and securely engage the inferior terminus of the canister containment section. The delivery nozzle section further demonstrates a rounded closed inferior terminus and a central bore especially configured and adapted to contain a docking port therein (as described, below). In certain examples of the second alternate embodiment of the present invention, a rotating delivery nozzle cap, as described below, is provided. In such embodiments, both side surfaces of the delivery nozzle section are especially shaped and configured to include, adjacent to the inferior terminus of the delivery section, rotation posts which mate with and engage nozzle cover rotation rings. The rotation rings, (as discussed below), enable the nozzle cover of such embodiments incorporating same to rotate so as to cover and uncover the collimation nozzle.

The delivery nozzle section of the second alternate embodiment includes a nozzle port located on the front surface thereof adjacent to the inferior terminus. The nozzle port is especially configured and adapted for secure engagement of the collimation nozzle of the present invention. The nozzle port is positioned upon the barrel shaped portion of the nozzle section so that it arises from the front surface of the device and opposite the rear surface midline alignment mark discussed above. This configuration enables a user who positions the device so that the midline alignment mark appears centered on the back surface of the device when positioned in a patient's nostril—and parallel to the midline of the patient's face—, to direct the collimated stream administered by the device directly into the patients nose, nasal antrum and nasopharynx without lateral or medial deviation. Such alignment, along with alignment of the device elevation alignment arrow/line discussed below with the tragus of the patient's ear, provides excellent targeting of the pharyngeal opening of the eustachian tube. The nozzle port may be positioned advantageously so as to depend downward at an approximately 135 degree angle as shown in the figures. Such angulation facilitates the ease of aligning the collimation nozzle, via the elevation alignment line/arrow formed within or upon the side surface of the delivery nozzle section, so that it is directed towards the patient's tragus after insertion of the nozzle into the patient's nose. This alignment provides excellent targeting of the pharyngeal opening of an infant's eustachian tube, as described above and below.

A housing junction provided between the superior terminus of the delivery nozzle section provides for a place of engagement of an inferior terminus of the canister containment section adjacent the inferior terminus. Within the central bore of the delivery nozzle section—and aligned with the housing junction opening thereof, the delivery nozzle section includes a docking port especially designed, shaped and configured to securely mate and engage with the distal portion of a canister, such as, for example, the constricted distal portion of a metered dose canister as well as the valve stem extending from the metering valve assembly therein. A conduit, which includes an opening at either end thereof, is formed within the docking port and runs continuously from the docking port to and through the nozzle port. This conduit provides a continuous fluid pathway and communication between the central bore of the valve stem when docked at the docking port—and the bore of the collimation nozzle affixed to the nozzle port—. An engagement sleeve may be advantageously utilized to join the administration nozzle with the canister containment nozzle.

End caps located lateral to the rotation rings cover, but do not rotate with the nozzle cover. In embodiments of the present invention utilizing rotating end caps, the elevation alignment line/arrows formed upon or within the side surfaces of the delivery nozzle section are advantageously positioned on such end caps in such a manner as to be in alignment with the collimation nozzle extending from the front surface of the second alternate embodiment of the present invention. Rotation of the rotation rings of the end cap assembly does not cause the elevation alignment arrows/lines to rotate.

In those examples of the second alternate embodiment not incorporating such rotating end caps, the alignment arrow/line are formed upon or within the side surfaces of the delivery nozzle section in a like manner, parallel to and in alignment with the longitudinal axis of the collimation nozzle. Such elevation alignment lines/arrows may be printed, raised or indented indicators. The elevation alignment lines/arrows are placed so as to be in alignment with the longitudinal axis of the collimation nozzle mounted upon the administration nozzle section as well as the collimated stream of any composition emanating therefrom. The term elevation alignment lines/arrows refers to the indicators formed upon or within the end caps providing alignment reference which may be formed of a simple straight line or a line with an arrowhead.

In practicing the method of the alternate embodiment of the present invention, a canister, such as, for example, a metered dose canister, filled with the appropriate and desired medication is placed within the administration housing so as to securely engage the docking port. In alternate embodiments of the present invention incorporating a rotating nozzle cover assembly, the nozzle cover is rotated away from the distal terminus of the collimation nozzle prior to each use so as to expose same for use.

Thereafter, the housing is securely engaged and held by a user utilizing the finger rests. Thereafter, the delivery nozzle is positioned within an external nasal orifice of a patient to receive the medication provided by the device. Thereafter the device is manipulated and positioned by a user until the elevation alignment line/arrow is positioned so as to point towards the tragus of the patient's ear. At the same time, the administration housing is aligned so that the midline alignment line is aligned with the midline of an infant's facial plane. Once the device is so positioned, the user pushes upon so as to depress the metered dose container further into the housing and against the docking port so as to cause the metered dose actuator valve to release a dose of the medication contained within the container so as to flow through the bore of the docking port and through the collimation tube. Since the elevation alignment line/arrow is aligned with an imaginary line running from the nasal orifice to the tragus, and the collimated stream flowing from the device is aligned with said same pathway, the stream of medication dispensed from the device is accurately directed towards the pharyngeal orifice of the eustachian tube.

The devices of the present invention may be advantageously formed of any medically approved material such as, for example, a medical grade plastic. It is preferred that such materials are selected to be easily sterilized by means of hot steam, ethylene oxide (ETO), plasma, gamma rays and STERRAD NX.

DETAILED DESCRIPTION

Figure 1:
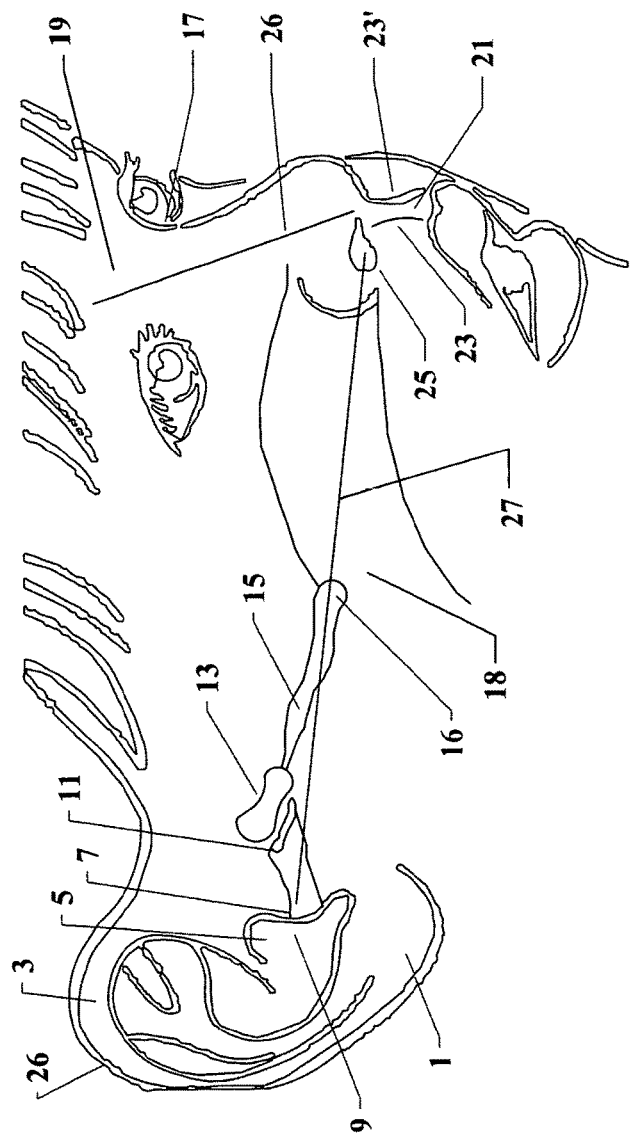
FIG. 1 is a drawing depicting internal structures of the ear, nose, throat and mouth of a child.

FIG. 1 illustrates the relative positions of several internal structures of the ear, nose, throat and mouth while also illustrating key—external—anatomical features of the child's face. The external structures of the ear 26 are illustrated including the lobule 1, the helix 3, the cavum conchae 5, a cup like depression located just anterior to the tragus 7. The tragus overlies a portion of the entrance to the external auditory meatus 9. As mentioned above, FIG. 1 also illustrates internal ear structures including the tympanic membrane 11 located and forming a barrier between the external auditory meatus 9 and the middle ear 13. The eustachian tube 15 is shown at its origin in the middle ear. It is further illustrated running—medially, anteriorly and inferiorly—to its lateral termination at the pharyngeal orifice 16 of the auditory tube 15 within the nasopharynx 18. FIG. 1 also illustrates the external landmarks of the nose including the bridge portion thereof 17. The location of the nasion 19, is also shown, an anatomical landmark where the two nasal bones and frontal bone intersection forming a surface depression in the facial feature. Just below the nose and above the upper lip, the philtrum 21 is also illustrated, a midline groove that runs vertically from the tip of the nose to the midline of the upper lip. Two philtral columns 23 and 23' are the relatively elevated facial ridges running parallel and at the lateral borders of the philtrum. One of the child's naris (nostril) 25 is also illustrated. FIG. 1 also includes a midline reference line 26 running along the midline of the illustrated face.

A nasal/tragus elevation alignment line, or, as it may also be called, with equal meaning, a nostril/tragus elevation alignment line 27 is a reference line demonstrating the relative linear relationship amongst the naris 25, the pharyngeal orifice of the eustachian tube 16 and the tragus 7 of the ear. The naris/tragus elevation alignment line 27 running from the nostril 25 to the tragus 7 intersects the pharyngeal orifice of the eustachian tube in regard to the elevational relationship thereamong. As described above, the device and method of the present invention, in addition to providing a well collimated stream of medication, is specifically designed and configured to enable an operator of the device to direct a focused stream of medication towards the eustachian tube's opening in the nasopharynx. As mentioned above, and discussed and illustrated in more detail, below, the nasal administration device of the present invention is designed, adapted and configured to deliver a well collimated stream of compounds, composition, and medicaments intended for delivery towards the pharyngeal orifice of the eustachian tube. More specifically, the disclosed device and method provide such effective and accurate delivery incorporating alignment tabs and elevation alignment line/arrows which enable a patient, or one administering such materials to a patient, to correctly position the device for an effective application of medications towards the eustachian tube orifice. The elevation alignment line 95, formed within or upon the sides of the delivery nozzle section of the housing, assist in positioning the administration device of the present invention so as to enable attainment of the correct elevation alignment of the collimated stream. In addition, the midline alignment line 58 formed upon or within the back portion of the housing enables a user to properly position the device so as to direct the collimated stream directly into the plane of the face—without substantial medial or lateral deviation—through the nasal passage towards the lateral wall of the nasopharynx at the level of the inferior nasal concha wherein the pharyngeal opening of the eustachian tube is located.

Figure 2:
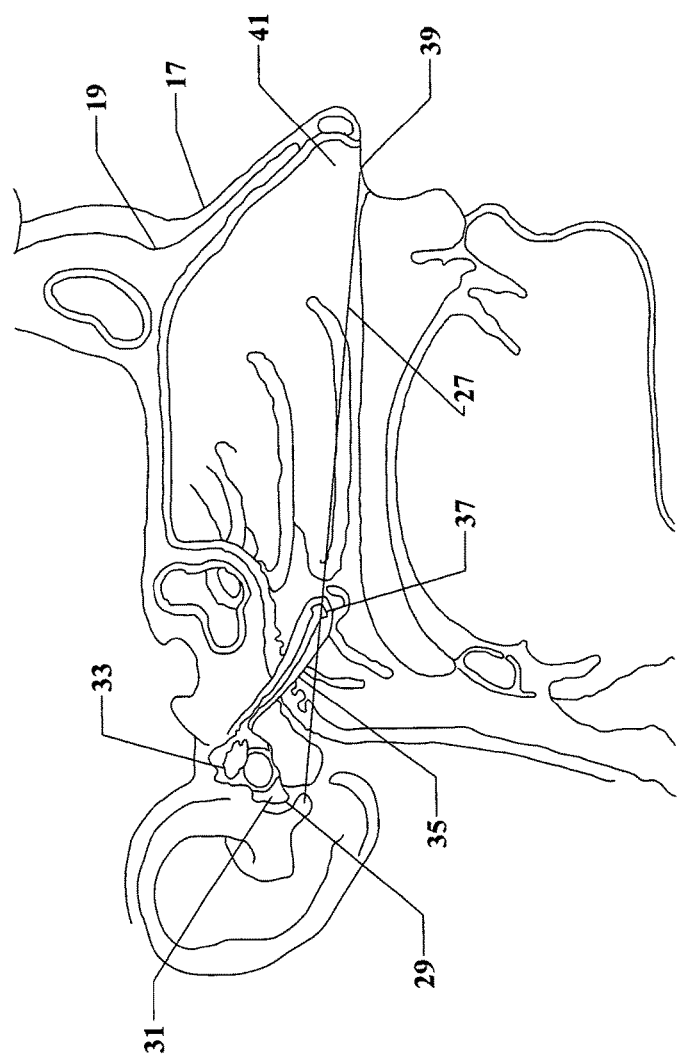
FIG. 2 is a drawing depicting internal structures of the ear, nose, throat and mouth of an adult.

FIG. 2 illustrates the tragus 29 of the external ear, the eardrum 31, the middle ear 33 and the eustachian tube 35 including the pharyngeal terminus thereof 37. FIG. 2 also illustrates a nostril 39 and the vestibule 41 to which it leads. Nasal/tragus elevation alignment line 27 shows the elevation alignment relationship in an adult of the naris 39, and the pharyngeal terminus of the eustachian tube 37. As is true in regard to FIG. 1 and the child's anatomy illustrated therein, alignment of the aforementioned three anatomical landmarks and structures, the tragus, nostril and pharyngeal opening of the eustachian tube—in regard to elevational alignment—, causes a collimated stream, originating at the nostril and aligned with the tragus of the ear, to closely approximate intersection with the region of the pharynx adjacent to the opening of the eustachian tube therein. As discussed above and below, the collimated stream is directed into the plane of the face, rather than in a medial or lateral direction, to attain further proper alignment in regard to medial/lateral alignment. If, for example, the facial plane is described as having a X axis running medially, from left to right, a "Y" axis running superiorly/inferiorly and a "Z" axis running directly into to the facial plane anteriorly/posteriorly, then the device of the present invention and the collimated stream provided thereby, is directed in alignment with both the "Z" axis—directly into the facial plane—and with the midline of the device in alignment with the "Y" axis, devoid of any cant.

Figure 3:
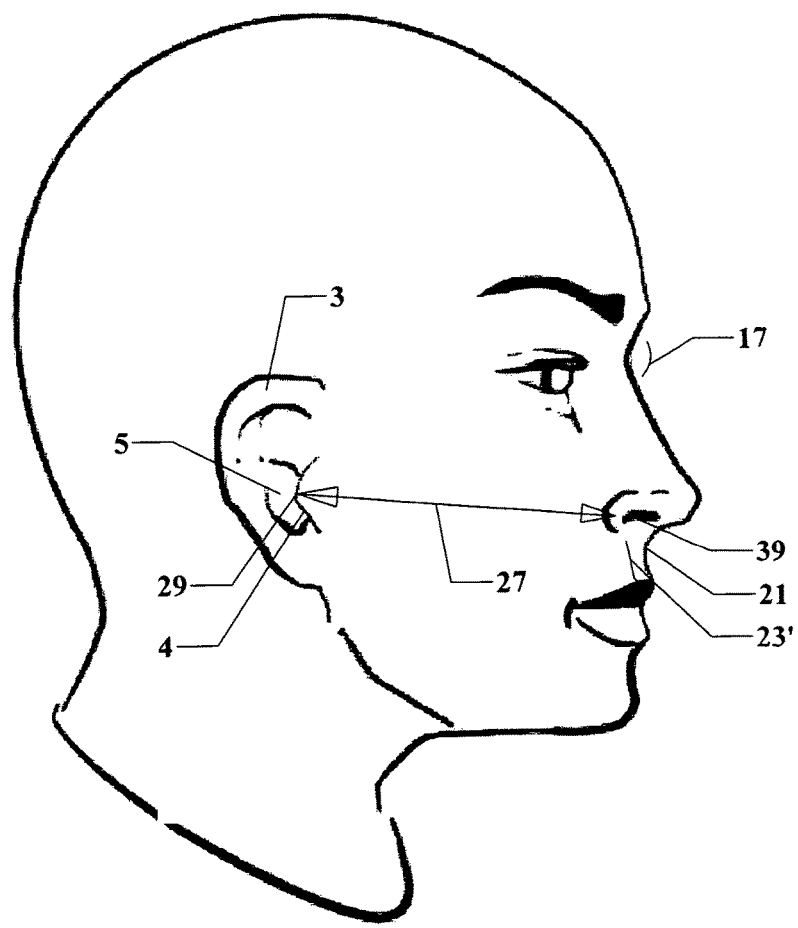
FIG. 3 is a drawing showing external landmarks only.

FIG. 3 is a profile view of an adult illustrating certain external anatomical landmarks. The helix 3, tragus 29, cavum conchae 5 as well as the entrance to the external auditory meatus 4 are shown. In addition, features of the nose including the right philtral column 23' the midline philtrum 21, nostril (naris) 39 and bridge portion 17 are illustrated. In addition, the naris/tragus reference (or, as it may also be referred to, naris/tragus elevation alignment line) 27 is also shown.

As discussed above, the delivery nozzle utilized in the device of the present invention, as well as the openings located at the proximal and distal termini thereof, demonstrate a uniform and constant diameter—without any constricted, enlarged or irregular portions thereof—in order to form a collimated stream. Such a configuration reduces lateral dispersion of compounds such as, for example, a mixture of lipid crystals, powders, liquids and mixtures thereof, released therethrough after activation of the nasal administration device providing such compounds. However, beyond forming the central bore of the delivery nozzle—as well as the distal and proximal termini thereof, so as to be constant and uniform in diameter—, -specific diameter ranges for said nozzle and termini can be advantageously selected, depending upon the content of the composition(s), materials and/or medications actually delivered by the device of the present invention to still further optimize collimation. For example, in regards to the aerosolized mixture of lipid crystals discussed above, specific diameters are preferred.

TABLE 1

| NOZZLE DIAMETER | SPRAY PATTERN DIAMETER | SPRAY PATTERN ANGLE |
| --- | --- | --- |
| 0.5 | 10.1 | 10.97 |
| 0.6 | 6.2 | 6.44 |
| 0.8 | 9.0 | 9.41 |
| 0.9 | 7.0 | 6.98 |
| 1.0 | 10.8 | 11.26 |
| 1.6 | 9.4 | 8.95 |
| 2.0 | 15.1 | 14.96 |

Metered dose canisters filled with (B33) and B2 and utilizing HFA 134A propellant were utilized to test the effect of nozzle diameter upon spray pattern collimation. For this purpose, the test canisters were fitted with 34 mm long administration nozzles having nozzle diameters (bores) ranging from 0.5 to 2.0 mm. Multiple activations and measurements were performed to provide the averaged data illustrated in Table 1, above. The canisters were activated in a passive environment devoid of any substantial air currents so as to simulate the method of the present invention which does not include active inhalation by the patient. More specifically, in practicing the method of the present invention it is highly advantageous to activate the metered dose canister and administer the collimated stream through a nostril between inhalation and expiration—while the patient is not actively breathing—or while the patient holds her breath—. The test was conducted indoors at a temperature of 80 degrees Fahrenheit under conditions provided to eliminate any substantial air current or draft that might otherwise interfere with the spay patters produced and deviate from the passive (non-inhalation) method of the present invention. The stream released from the nozzle was directed towards an absorbent paper target 50 mm from the terminus of the test nozzles.

As noted in Table 1, above, a 0.6 mm nozzle resulted in the most concentrated spray pattern with a dispersion angle of only 6.44 degrees. The 0.6 degree diameter nozzle also produced a relatively diminutive pattern formation of 6.2 mm at 50 mm from the terminus of the nozzle. Generally, nozzles demonstrating a diameter of from 0.6 to 0.9 with dispersion angles ranging from 6.44 to 9.41 degrees. This same diameter range of 0.6 to 0.9 mm resulted in a spray pattern diameter of from a minimum of 6.2 mm to a maximum of 9.0 upon the target 50 mm distant from the tip of the collimation nozzles. At the smallest and largest diameters tested, collimation deteriorated. The preferred nozzle diameters ranged from 0.6 to about 0.9 mm which provide the tightest collimation.

As mentioned above, the device and method of the present invention incorporates a collimation nozzle demonstrating a uniform and constant diameter so as to improve the delivery of medications to the pharyngeal orifice of the eustachian tube by reducing wasteful and inefficient scattering of the spray. Specific bore/opening diameters may be advantageously selected to further improve collimation for each specific composition delivered.

Figure 4:
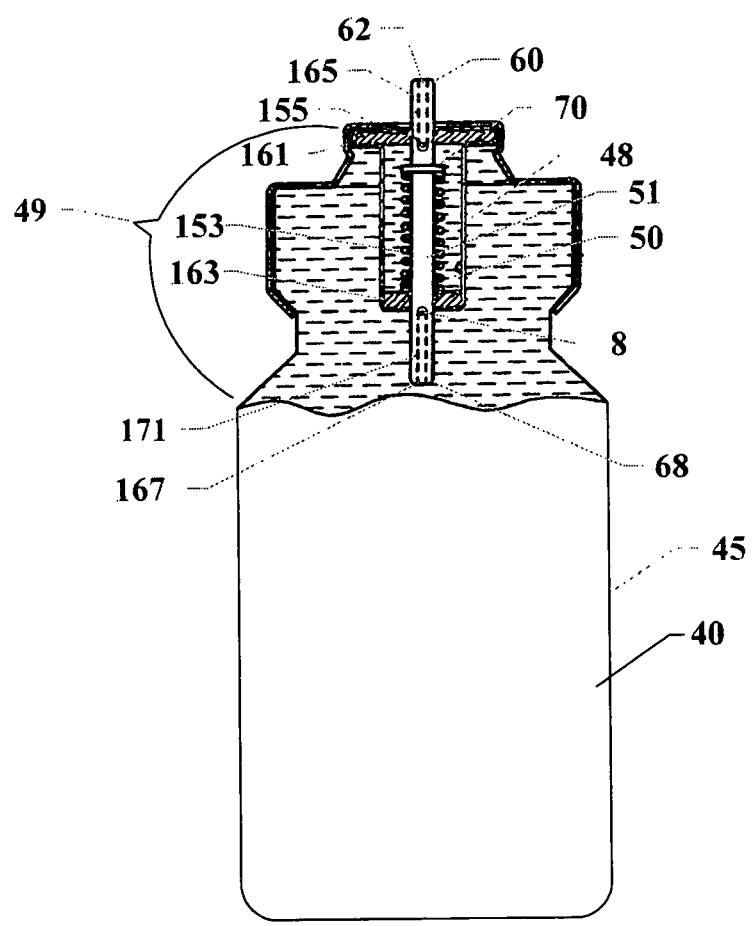
FIG. 4 illustrates a sectional view of a metered valve canister suitable for use in the present invention.
Figure 5:
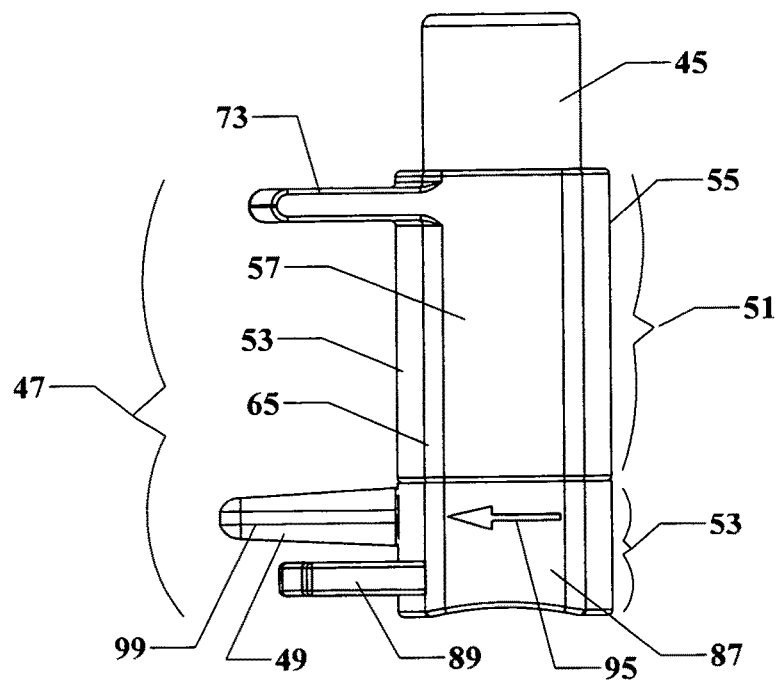
FIG. 5 is a side view of the first preferred embodiment of the present invention
Figure 6A:
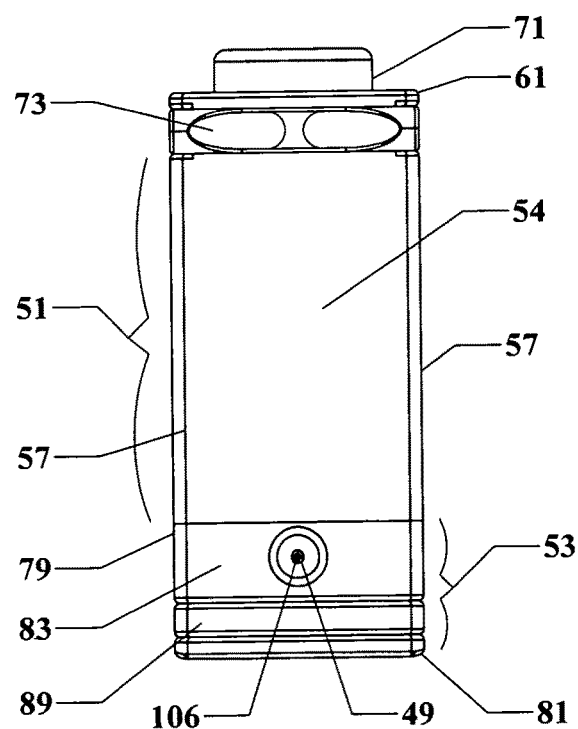
FIG. 6*a* is a front view of the first preferred embodiment of the present invention
Figure 6B:
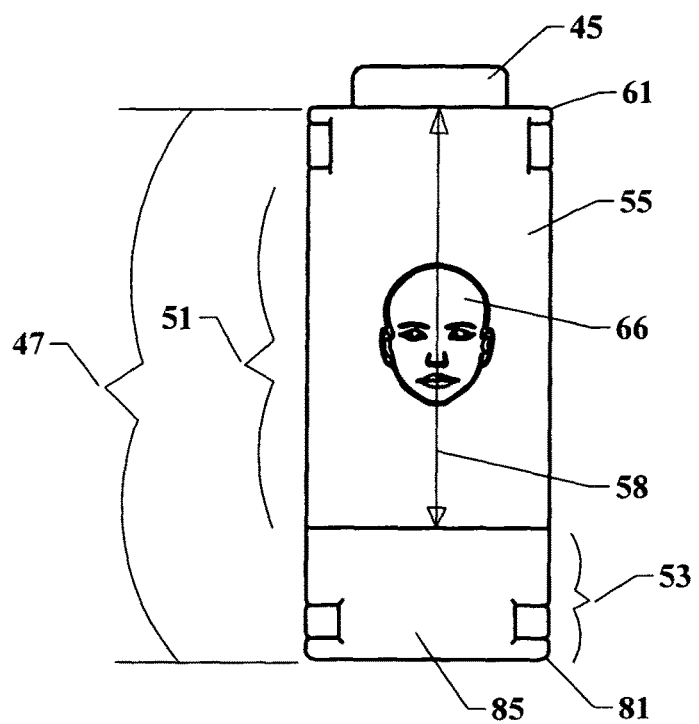
FIG. 6*b* is a rear view of the first preferred embodiment of the present invention.
Figure 7:
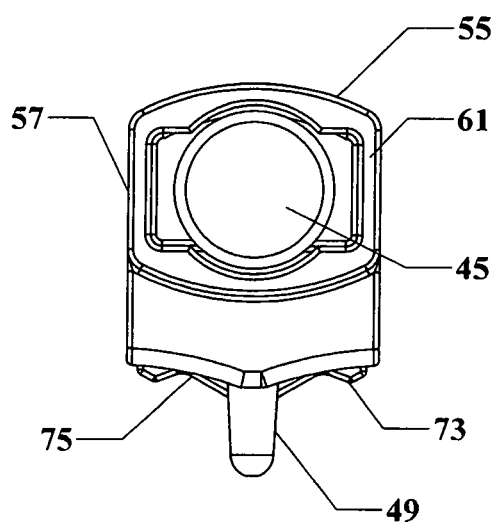
FIG. 7 is a top view of the first preferred embodiment of the present invention

FIG. 4 illustrates a sectional view of a metered valve canister suitable for use in the present invention. The metering dose canister 45 includes a main chamber 47 which is filled with a compound to be delivered to a patient. A constricted section 52 is especially shaped and configured for receipt of a metering valve 48. The metering valve includes a metering chamber 50, a valve stem 51, and a return spring 53. Chamber gaskets 61 and 63 form seals at the distal and medial terminus of the metering chamber. The valve stem includes a distal 55 and medial 57 metering chamber apertures. The distal metering chamber aperture is in fluid communication with an opening 62 at the distal terminus 60 of the stem via the distal stem conduit 65 which forms a bore through the distal portion of the valve stem. The medial metering chamber aperture 57 is in fluid communication with the medial stem aperture 67 located at the medial terminus 68 of the valve stem via medial stem conduit 72.

Prior to actuation, the return spring 53 biases against the stem return stop 73 so as to extend the stem distally, out from the canister until the return ring comes into contact with the distal canister gasket 61. In this position, the medial stem conduit, located within the mesial portion of the stem, forms a pathway between the main canister chamber 47 of the canister bottle and the metering chamber 50 and thus fills the metering chamber with a predetermined amount of compound. The metering chamber acts to control (meter) the amount of vessel contents released upon each actuation. In order to actuate the canister, the stem is depressed into the canister which compresses the return spring 53 and causes the medial metering aperture 57 to pass medially into the main chamber—thereby closing off fluid communication between the main chamber and the metering chamber—. Distal movement of the stem also causes the distal metering aperture 55, ordinarily located distal to the metering chamber, to come into fluid communication with the metering chamber and the contents therein. Such movement enables the distal stem conduit 65 to conduct the contents of the metering chamber from the canister due to the boiling of the chamber contents upon contact with atmospheric pressure enabled by the opening of the distal conduit. The pressurized formulation that had been measured and contained within the metering chamber is then released rapidly into the distal conduit 65 of the valve stem, which, together with the stem conduit, forms an expansion chamber in which the propellant begins to boil. The canister is ordinarily utilized in the inverted position, with the valve located at the proximal end of the canister—, below the container so that the valve will refill under gravity. Virtually any type of canister bottle of the prior art may successfully and advantageously utilized in practicing the present invention so long as the administration housing is shaped and configured to properly mate with such canisters and such canister can be actuated when placed within the administration housing.

FIGS. 5-8c illustrate the first preferred embodiment of the present invention. The example of the first preferred embodiment illustrated in these figures, (as well as the first alternate preferred embodiment, discussed below) is configured for a metered dose canister bottle 45. The device is comprised of an administration housing 47 and a collimation nozzle 49. The administration housing 47 of the first preferred embodiment of the present invention is illustrated in FIG. 5 through FIG. 8c. The administration housing is comprised of a canister containment section 51 and a delivery nozzle section 53. The canister containment section 51 of the housing is an elongated hollow structure having a front wall 54, rear wall 55 and two side walls 57. The rear wall of the canister containment housing may advantageously include a midline alignment line 58 running along the midline of the front wall and parallel to the long axis of the canister containment section and the central bore thereof. It is still further advantageous and preferred to superimpose the midline alignment line 58 formed upon an outline of a face 66 formed upon, within or otherwise at the rear wall 55. The pictograph illustrated in FIG. 6b shows the midline alignment line 58 superimposed upon the midline of a patient's face which enables a user to, not only align the device properly with the facial midline, but to also understand the location of the midline of the face referred to. Once the midline landmark is understood, a user merely positions the device so that the midline alignment line formed upon or within the rear wall of the housing is parallel to the facial midline.

The canister containment section also includes openings 59/59' located at the superior 61 and inferior termini 63 thereof. A large central bore 65, having a longitudinal axis 67, runs the longitudinal length 69 of the canister housing and is continuous with the openings at the superior 59 and inferior 59' termini thereof.

The large central bore of the canister containment section is designed and configured to demonstrate a shape and size which enables placement and retention therein of a canister bottle 45. For this purpose, the superior terminus 61 of the housing is especially shaped and configured to define an opening of sufficient size and shape so as to enable passage therethrough of the canister bottle for which the housing is configured. The inferior terminus 63 of the housing is shaped and configured to define a shape and opening which enables mating engagement thereof with the superior terminus 79 of the delivery nozzle section 53 of the housing. The length of the administration housing 69 is advantageously selected to be such as to enable a small portion of the metered dose canister, —the distal end 71 thereof—to extend beyond the superior terminus of the housing. This slight extension of the canister beyond the superior terminus of the housing provides easy access for depressing the canister into the administration housing for device activation as discussed in detail, below.

Figure 8A:
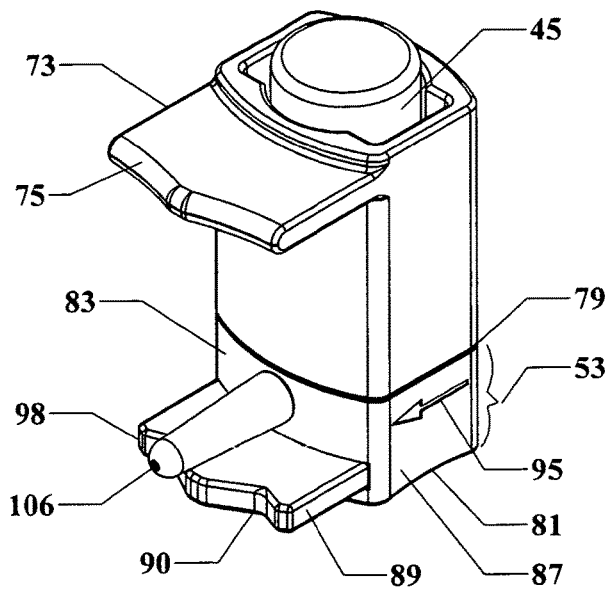
FIG. 8*a* is a front isomeric view of the first preferred embodiment of the present invention.
Figure 8B:
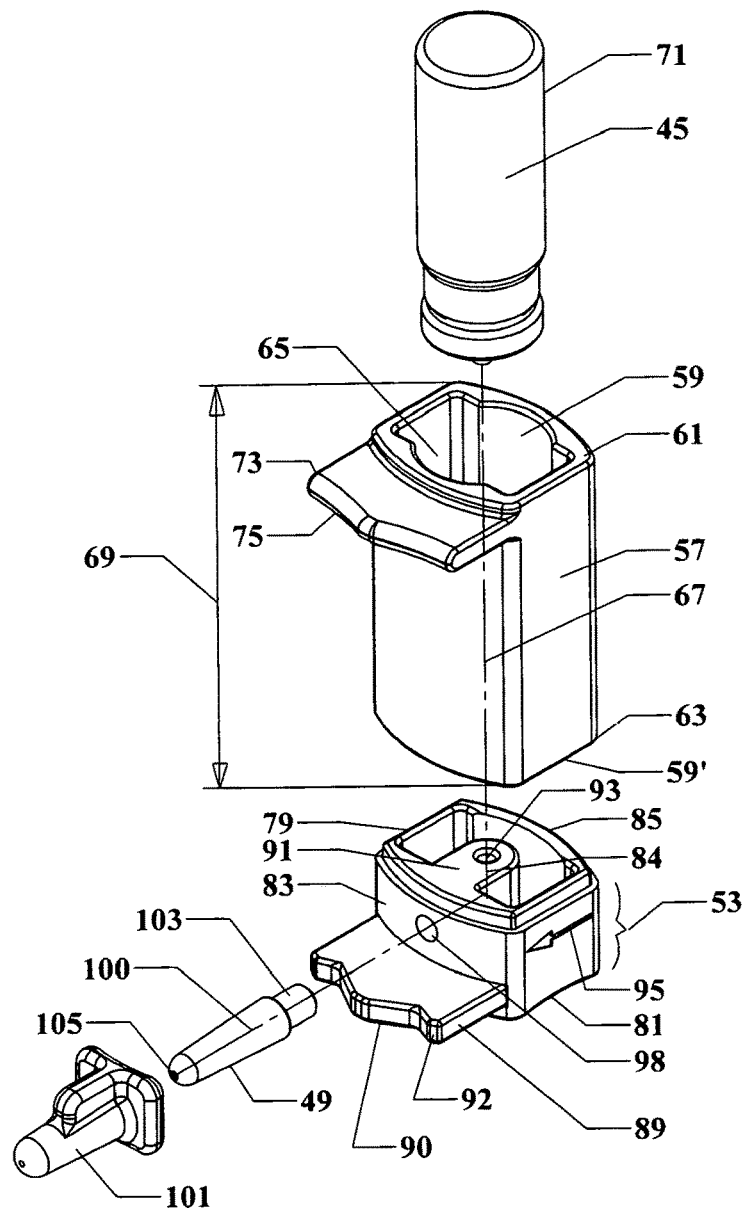
FIG. 8*b* is an exploded view of FIG. 8.
Figure 8C:
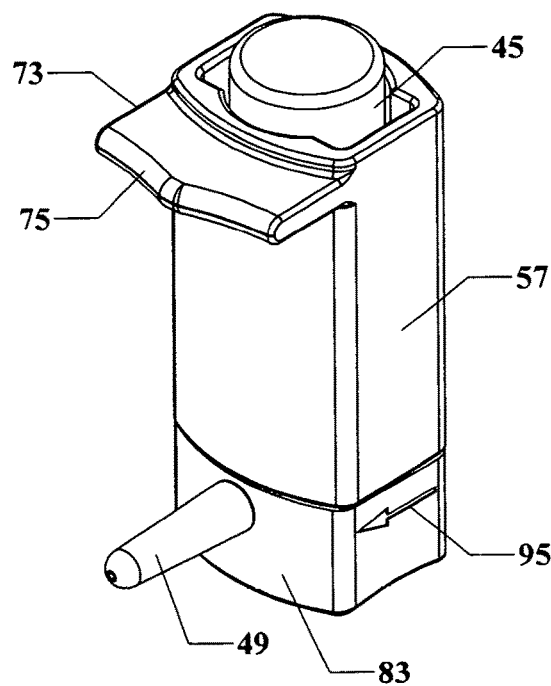
FIG. 8*c* is a front isomeric view of an example of the first preferred embodiment not including a delivery section alignment tab.
Figure 9A:
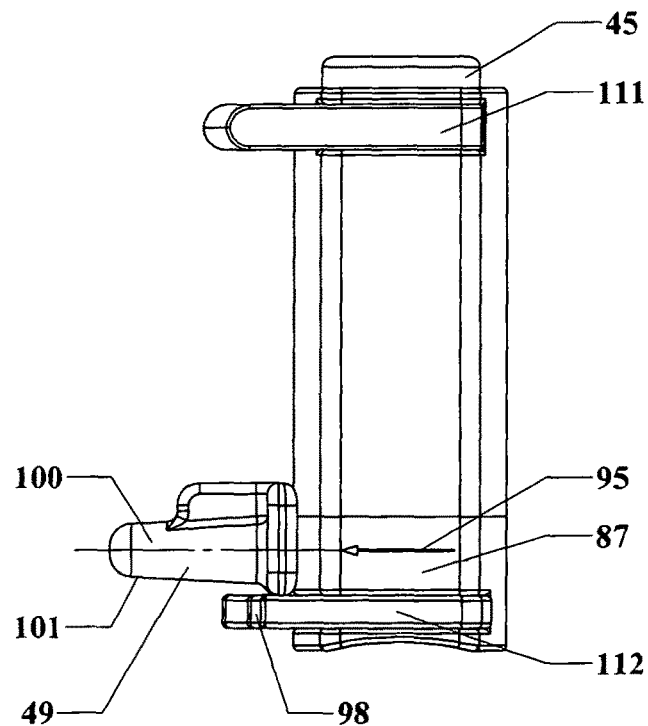
FIG. 9*a* is a side view of the first alternate embodiment with adjustable tabs.
Figure 9B:
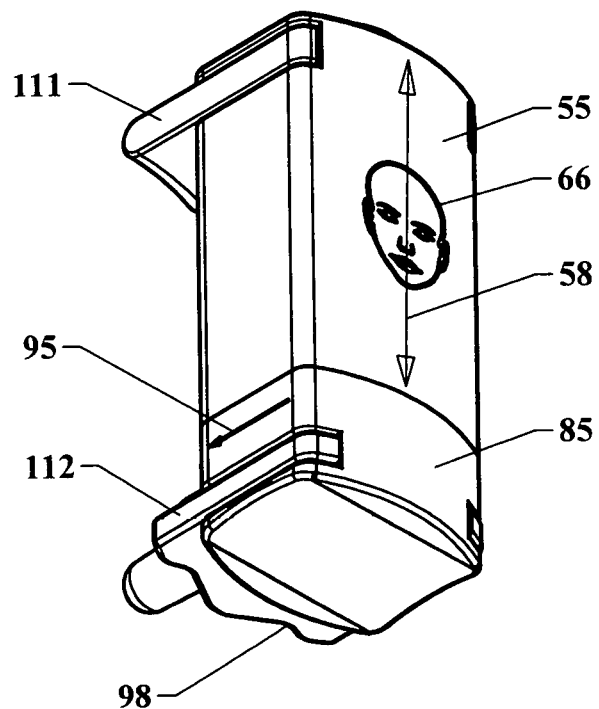
FIG. 9*b* is a rear isomeric view of the embodiment shown in FIG. 9*a*.
Figure 10A:
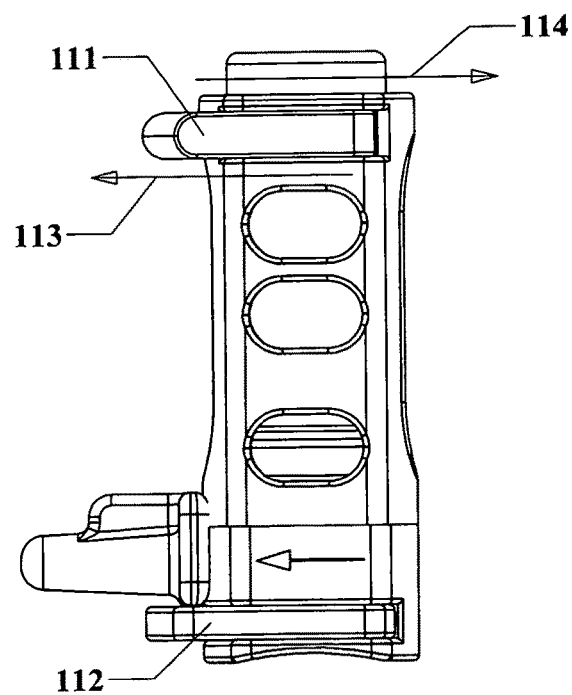
FIG. 10*a* is a side view of another example of the first alternate embodiment with a nozzle cap
Figure 10B:
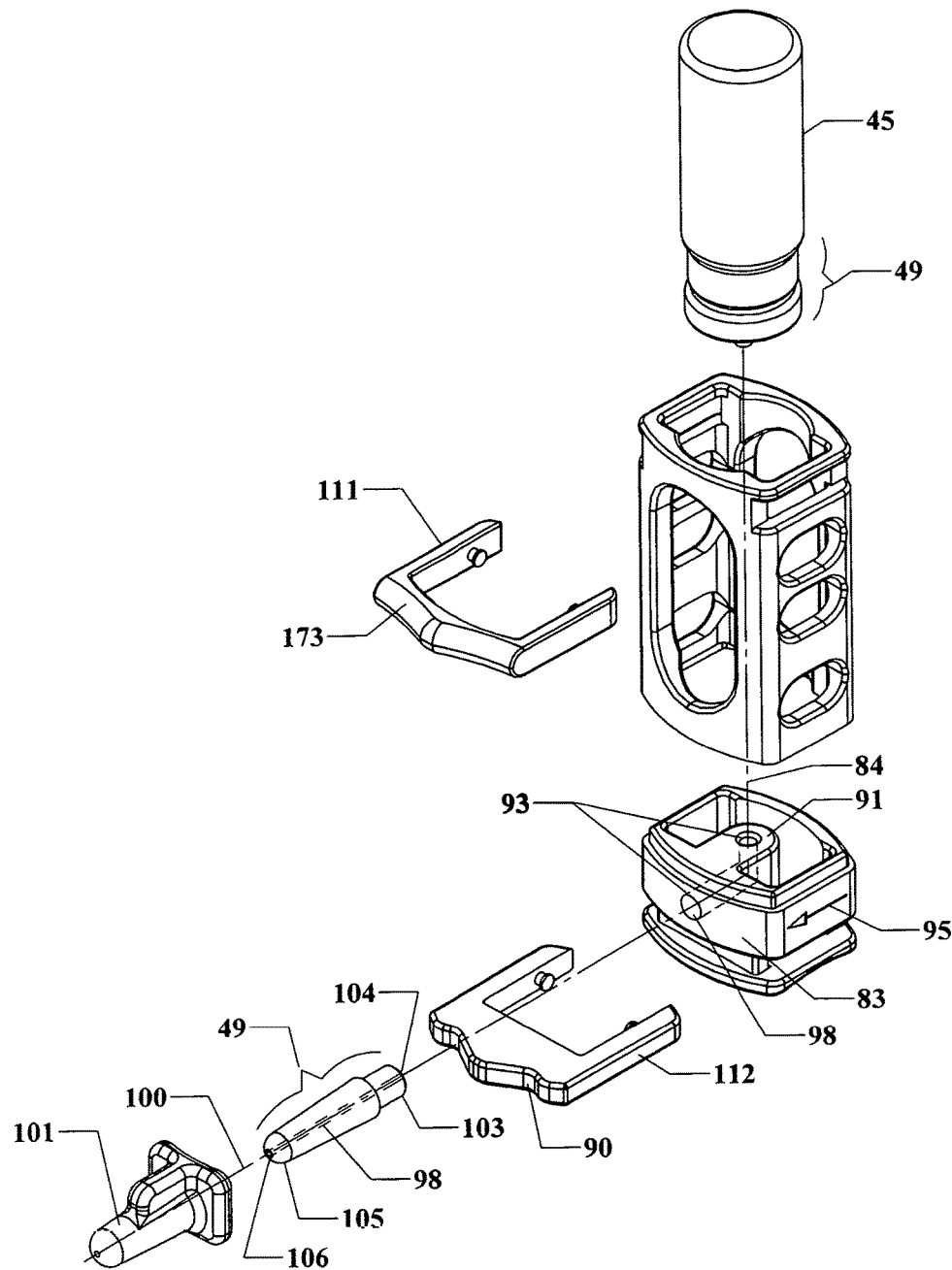
FIG. 10*b* is an exploded view of the embodiment illustrated in FIG. 10*a*.
Figure 10C:
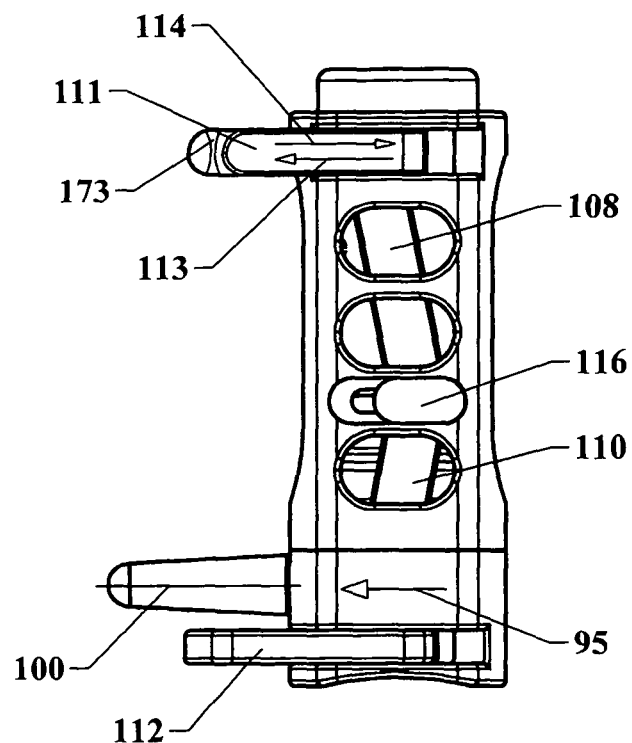
FIG. 10*c* is a side view of the first alternate embodiment with an alignment tab locking mechanism.

Adjacent to the superior terminus of the canister containment section, a containment section alignment tab 73 is provided. The tab is mounted so that it extends from the front wall of the canister containment section of the housing at approximately 90 degree angle relative to the longitudinal axis of the canister section and is located adjacent to the superior terminus 61 of the canister containment housing. Alternate preferred embodiments of the present invention, as illustrated in FIGS. 9a, through 10c advantageously incorporate adjustable canister alignment tabs. In such configurations, the tab is mounted to the canister containment section in such a manner as to allow the tab to extend away, and retract towards the front wall of the housing. FIGS. 5-8c illustrate the first preferred embodiment utilizing non-adjustably mounted alignment tabs. The size, length and configuration of both the fixed and adjustable (e.g., non-sliding, and sliding superior canister section alignment tabs) are designed so as to enable stable placement of a distal—contoured portion—75 of the alignment tab against the root portion 17 of the nose, while simultaneously placing the delivery nozzle within a patient's nostril. The present invention also contemplates a delivery device which includes only one alignment tab, a canister containment section alignment tab 73, as illustrated in FIG. 8c. Such alternate embodiments also contemplate incorporation of a single adjustable canister alignment tab—such as a slideable canister section alignment tab in addition to embodiments demonstrating a single fixed alignment tab as illustrated in FIG. 8c. In such embodiments, the canister containment alignment tab functions in the same manner as discussed herein in regard to stabilizing the position of the administration housing. However, in such embodiments, rather than utilizing a delivery nozzle section tab, the delivery nozzle itself functions as a second point of stabilization.

Figure 11A:
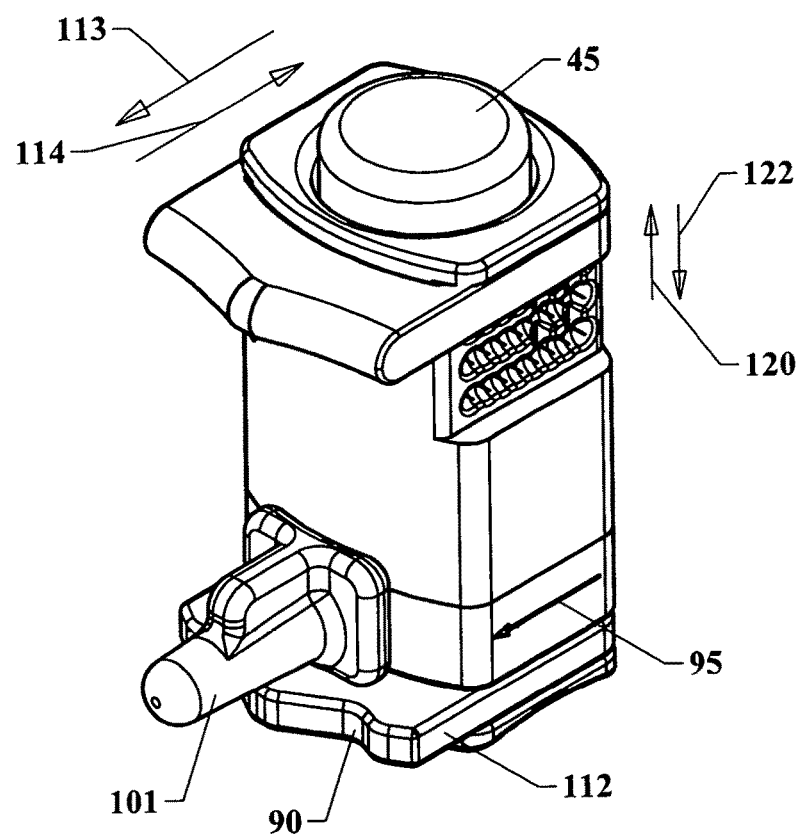
FIG. 11*a* is a front isomeric view of the first alternate embodiment of the present invention having a longitudinally adjustable canister alignment tab.
Figure 11B:
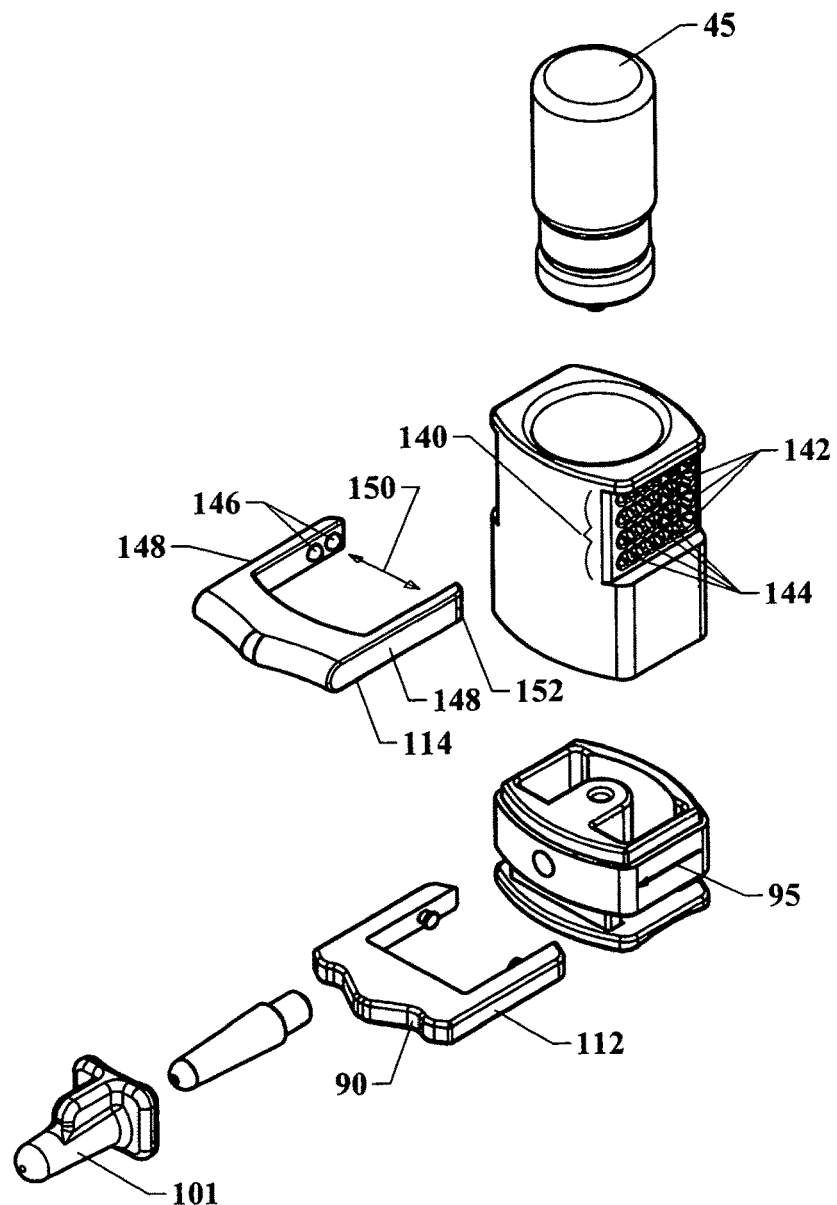
FIG. 11*b* is an exploded view of the embodiment illustrated in FIG. 11*a*.
Figure 11C:
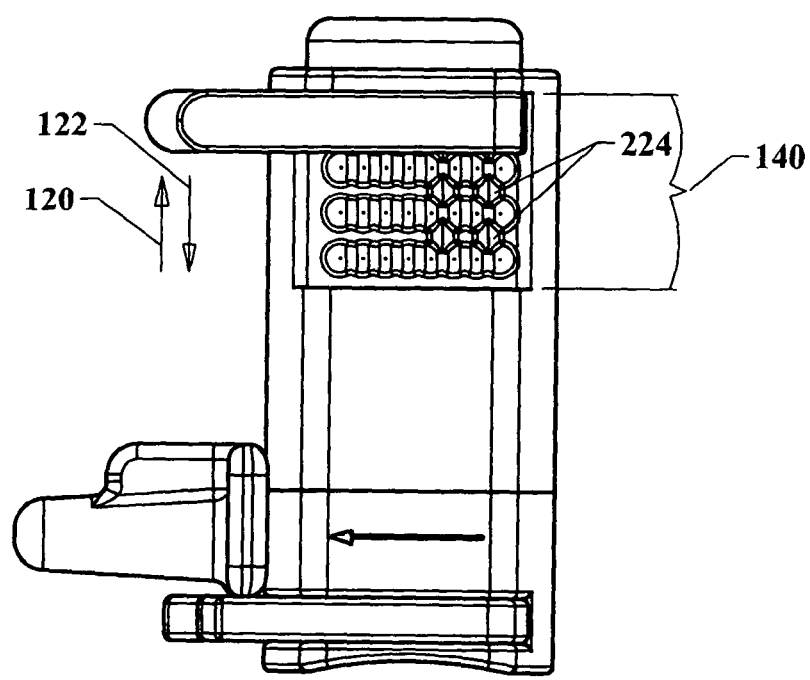
FIG. 11*c* is a side view of the embodiment illustrated in FIG. 11*a*.

As mentioned above, the first preferred embodiment, as well as the first alternate embodiment of the present invention may also incorporate fixed delivery nozzle section alignment tabs 89 or adjustable delivery nozzle section alignment tabs 112 which are especially shaped and configured to form stable contact with a patients face in the region of philtral columns 23/23" via contoured surfaces 90. The length of the canister section tabs as well as the delivery section tabs are especially selected so that, when the canister section alignment tab is placed into contact with the root portion of a patient's nose, and the delivery section alignment tab is placed into contact with a philtral column, the collimated stream emanating from the device upon activation is directed towards and in close proximity with the pharyngeal opening of the eustachian tube. The tabs are so configured and adapted to provide such accurate targeting for a majority of child and adult facial configurations, shapes and sizes. However, and as discussed in more detail, below, the first alternate preferred embodiments of the present invention incorporate the above-mentioned adjustable (or, e.g., slideably mounted) canister containment section alignment tabs and, in some embodiments, adjustable delivery nozzle section alignment tabs so as to provide greater application of the device to a wider range of patient facial shapes and sizes. Such adjustable tabs can be extended away and retracted towards the canister section and delivery section to finely tune angulation of the longitudinal axis of the delivery nozzle bore toward the pharyngeal opening, (or as it may also be referred to, the stoma of the eustachian tube) utilizing the guidance provided by embodiments of the present invention which incorporate elevation alignment line/arrow 95 formed within/upon or otherwise created upon the side walls delivery nozzle section. Furthermore, as illustrated in FIGS. 11*a* and 11*b*, certain examples of the first alternate embodiment of the present invention include canister section alignment tabs that adjust longitudinally, along the length of the canister section, as discussed below. In addition, the administration housing of the device may be provided in several different lengths so as to accommodate, for example, young children, older children and adults. More specifically, the increasing distance between the philtral columns and root sections of the nose of such groups would be expected. Therefore, it would be advantageous to provide administration housing in several sizes configured for such patient population groups. More specifically, such administration housing would be selected to demonstrate distances between the canister alignment tab and the delivery section tab which correspond to the average distance of the philtral column and root section of the nose of such groups. Such variations in such distances are also accommodated by means of the longitudinally adjustable canister alignment tabs illustrated in FIGS. 11*a*, 11*b* and 11*c*, below.

The delivery nozzle section 53 of the administration housing of the present invention includes a superior terminus 79, inferior terminus 81, a front section 83, a back section 85 and two side sections 87/87'. A longitudinal axis 84 of the delivery nozzle section runs from the inferior and distal terminus and is in alignment with the longitudinal axis of the canister containment section. The superior terminus 79 of the nozzle delivery section is open and is especially shaped and configured so as to enable secure mating thereof with the inferior terminus 63 of the canister containment section. Located within the nozzle delivery section and adjacent to the superior terminus 79 thereof, a canister docking port 91 is formed and provides secure insertion of and matting with the constricted section 52 of the canister bottle as well as the valve stem 51 extending from the metered dose valve. The nozzle docking port is designed and configured to provide fluid connection, by means of conduits 93 formed within the docking port, with an delivery nozzle port 95 formed upon and/or within the front portion 83 of the delivery nozzle section. The delivery port 95, in turn, is especially shaped and configured to matingly engage and form fluid communication with a delivery nozzle 49 as well as the central bore 98 formed therewithin. Although the preferred embodiment illustrated herein utilizes separate canister containment sections and delivery nozzle sections, configurations of the device are also contemplated wherein such sections are formed as one unified housing.

The collimation nozzle 49 includes a central bore 98 demonstrating a constant, continuous and uniform diameter. In embodiments utilized for administration of a specific composition, identified diameter ranges are utilized to further enhance collimation—as discussed above and below in regard to the aforementioned mixture of lipid crystals—which further optimizes the collimation of a stream of an administered compound for optimal delivery of such to the pharyngeal orifice of the Eustachian tube. The nozzle includes a proximal 103 and distal 105 termini which include openings 104 and 106 which are equal in diameter to the central bore 98 and in fluid communication therewith.

Once delivered to that portion of the nasal pharynx, adjacent to and in the vicinity of the eustachian tubes pharyngeal orifice, the mixture of lipid crystals, discussed above, can easily enter and form a spread film upon the aqueous layer residing upon the epithelial lining of the auditory tube. The devices of the present invention are especially configured and adapted, when utilized in accordance with the method of the present invention, to deliver a collimated stream of compound(s), composition(s) and/or medication(s) to the nasal pharynx so that the collimated stream is deposited upon the posterior mucosa of the nasopharynx within a radius of 15 mm of the nasopharyngeal orifice of the eustachian tube. Thereafter, the composition is able to quickly reach and enter the eustachian tube through it nasopharyngeal orifice.

The proximal terminus 103 of the actuator collimation nozzle 49 is mounted upon and within the delivery nozzle port 98 in such a manner as to orient the longitudinal axis 100 of the central bore 99 of the nozzle thereof in a 90 degree relation with the longitudinal axis of the canister and delivery sections. A delivery nozzle cap 101 may also be optionally provided so as to keep foreign matter from entering into the distal end of the delivery nozzle when not in use.

A delivery nozzle section alignment tab—fixed 89 or adjustable 112—may be advantageously located and positioned adjacent to the inferior terminus of the delivery nozzle section. The delivery section alignment tab may advantageously arise from the front portion 83 of the delivery section perpendicular to the longitudinal axis 84 of the delivery nozzle section. The delivery nozzle section alignment tab arises from the front wall 83 of the delivery nozzle section just below the delivery port and collimation nozzle 49 extending therefrom. This alignment tab is positioned adjacent to the inferior terminus 81 of the delivery section. The delivery section alignment tab advantageously includes a contoured portion 90 at the distal terminus thereof which is especially contoured so as to enable close adaptation and contact above a patients upper lip in the region of philtrum 21 upon, for example a philtral column.

As described below, certain preferred embodiments of the present invention include elevation alignment lines 95, or, as they also may be referred to, equally and with the same meaning herein, elevation alignment arrows, formed within or upon the side walls of the delivery nozzle section of the housing. Such lines may also be simply printed in that location. The elevation alignment lines/arrows are positioned so as to be parallel to and in alignment with both the longitudinal axis 100 of the collimation nozzle 49 as well as the collimated stream of fluids/powders emanating therefrom. The present invention also contemplates embodiments devoid of such elevation alignment lines/arrows which utilize the canister section alignment tab and delivery nozzle positioning, with and without position of a delivery section alignment tab, to provide proper alignment of the collimated stream of compound(s) emanating from the device with the pharyngeal orifice of the eustachian tube.

As described in more detail below and illustrated in FIG. 9*a* through 11*b*, the first alternate preferred embodiments of the present invention include and incorporate an adjustable—e.g. slidably mounted—canister section alignment tab 111. Such slideable alignment tabs extend outward 113 as well as retract inward 114 so as to allow precise alignment of the administration housing to a wider range of facial contours and profiles. In the preferred embodiments illustrated in FIGS. 9*a* through 11*b*. an adjustable delivery nozzle section alignment tab 112 is also incorporated into the delivery device providing even further adjustability of the position of the device. However, the present invention contemplates embodiments with any combination of fixed and adjustable canister and/or delivery section alignment tabs. In addition, as discussed above and illustrated in FIG. 8c, the present invention contemplates embodiments utilizing just one alignment tab.

In the embodiment illustrated in FIG. 10c, control arm struts 108 and 110 are pivotally affixed at their distal termini to slideable alignment tabs 111 and 112 respectively. Each of the two control arm struts are pivotally affixed, at their proximal termini, to locking control actuator control 116. Depressing the locking control actuator into the housing enables manual adjustment—retraction/extension—of the adjustable alignment tabs. Once a desired position is attained, the actuator control is released and a return spring biases the control outward so as to lock the actuator and prevent further movement (sliding) of the alignment tab(s). In certain preferred embodiments of the present invention, only the canister containment section alignment tab is adjustable. In other embodiments, as illustrated in FIGS. 9a through, 10b, both tabs are adjustable and are so arranged and configured to maintain, with substantial resistance, passive change in a position set by a user. Such resistance to passive movement may be provided in various ways, known to the art, including, as discussed, immediately below, the use of alignment tabs demonstrating elastic memory sufficient to enable the tabs to be expanded for adjustment and then to immediately return, due to said memory, to a stable pre-expansion state wherein there position upon the housing is fixed.

FIGS. 11a and 11b illustrate examples of the first alternate preferred embodiment provided which includes an additional example of an adjustable canister section alignment tab 102 providing greater adjustability. More specifically, canister alignment tab 102 adjusts for both extension 113 and retraction 114, as well longitudinal adjustment so as to enable the tab to be moved in a proximal 120 as well as a distal 122 direction. In the embodiment illustrated in FIGS. 11a and 11b, tab adjustment recess 140 includes multiple parallel horizontal adjustment grooves 142 arranged along the side walls of the canister section. Each of the adjustment grooves includes a plurality of lock bores 144 arranged in a linear fashion along each groove. These lock bores act as detents for two pairs of adjustment pins 146 formed on inner opposing surfaces of each of the two parallel locking arms 148 of alignment tabs 114 adjacent to the proximal terminus 152 thereof. The parallel locking arms 148 demonstrate sufficient flexibility and elastic memory so as to enable the arms to be expanded 150 by a user. Such expansion enable the alignment tab to be moved proximally (upward) 120 or distally (downward) 122 from one horizontal groove to another via a parallel pair of longitudinal adjustment grooves 224 in order to adjust the longitudinal position of the tab. The adjustment pins are advantageously formed as round projections with diminishing diameter as they extend from the inner surface of the parallel locking arms. Retraction or extension force applied by a user to the tabs causes the two parallel locking arms to expand as the rounded pins are forced out of locking bores and then, due to the elastic memory of the parallel locking arms, into adjacent selected bores so as to enable one to adjust the retraction and or extension of the tab into a desired position. Extension of the alignment arm completely out an adjustment groove allows a user to position the arm in a more proximal or distal level groove in accordance with the distance between a patient's nostril and bridge portion of the patient's nose. Although this is one example of a configuration useful for providing longitudinal adjustability for the canister section tab, it is by no means limiting to the scope of this invention.

Figure 12:
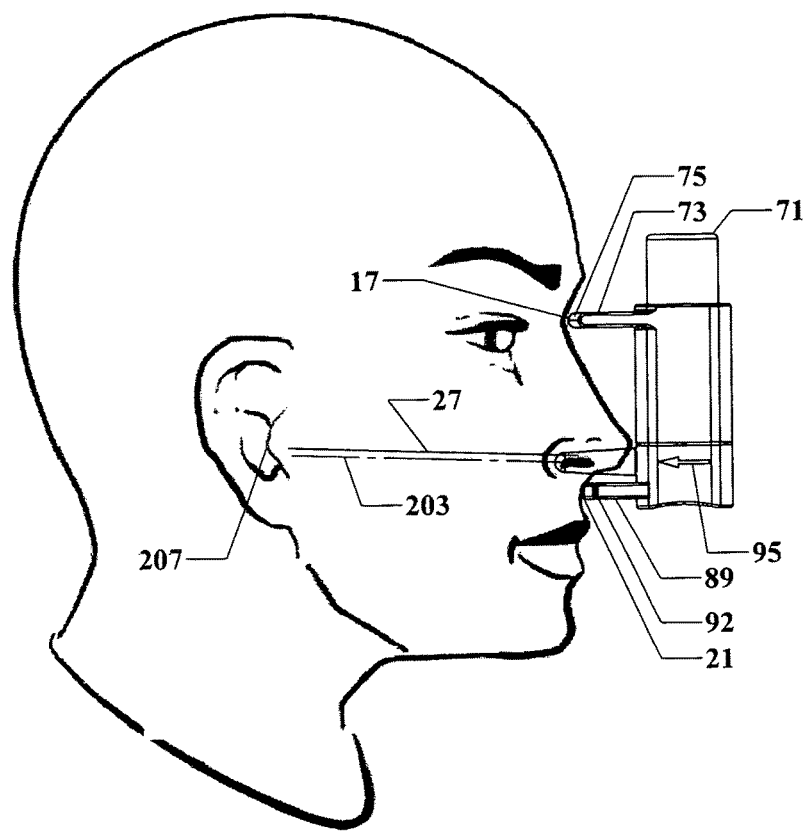
FIG. 12 is a side view of the first preferred embodiment shown in a correct working position upon a patient.
Figure 13:
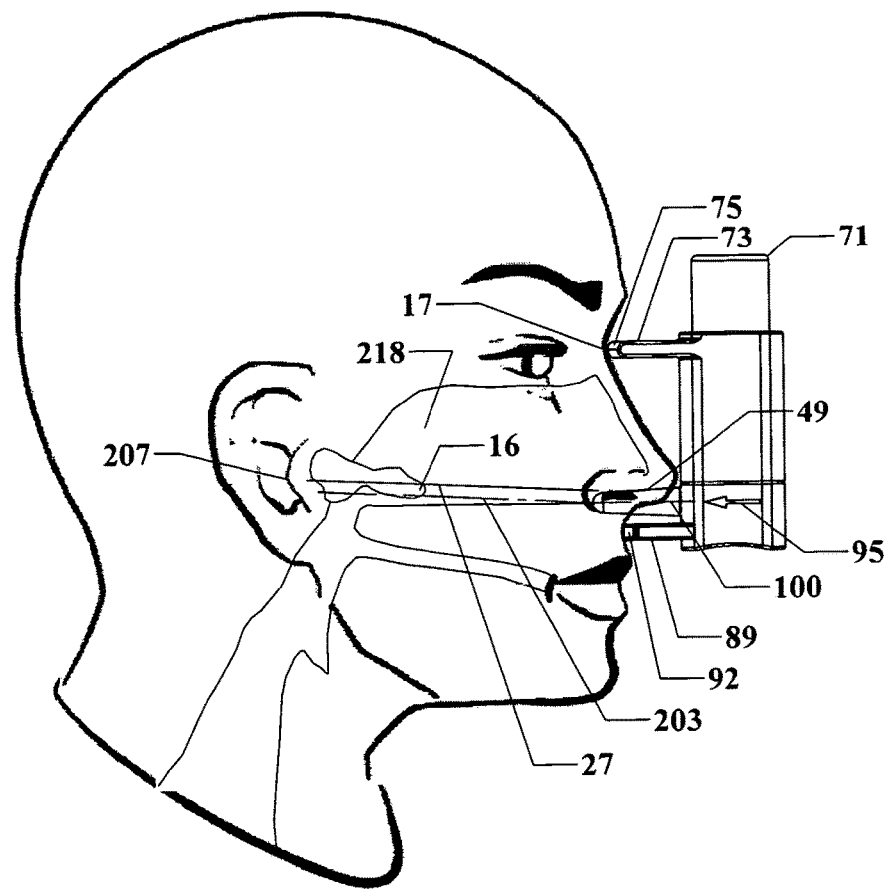
FIG. 13 illustrates a side view of a patients face depicting some of the internal structures of the ear, nose, throat and mouth with the preferred embodiment of the present invention placed in a correct operational position (FIG. 1).

FIGS. 12 and 13 illustrate a side view of a patients head in which the preferred embodiment of the nasal administration device of the present invention is correctly placed and aligned (FIG. 12) and illustrative some of the internal structures of the nose—the tragus 207, pharyngeal orifice of the eustachian tube 16, the nasopharynx 218 the mouth and throat (FIG. 13) with additional illustration of the path of the collimated stream 203 emanating from the collimation nozzle. The naso/tragus reference line 27 is also illustrated. In practicing the preferred method of the present invention, a canister bottle filled with a compound(s), mixture(s) and/or medication to be delivered is securely inserted into the administration housing. The canister is docked within the administration housing so that a valve stem extending therefrom as well as a distal portion of the canister bottle are in mating engagement with the docking port and are in fluid communication with the conduit within the docking port. The collimation nozzle 49 is then placed in an external nasal orifice of a patient with the canister section alignment tab positioned against the bridge of the nose, and, if the embodiment inclusive of one, the delivery nozzle section alignment tab placed above the upper lip upon a philtral column (on the same side of the patients face as the nostril entered). This placement ordinarily results in a delivery device position that orients the elevation alignment line/arrow formed in or upon the side walls of the delivery nozzle section of the housing so that it points to the tragus of the patient (on the same side of the face as the nostril in which the device is inserted. Thus, the elevation alignment line/arrow is placed in alignment with, in regard to elevation, with the naris/tragus reference line 27 discussed above. As discussed in much greater detail below, positioning the administration device and activating it in this manner results in directing a collimated stream emanating from the device so as to closely approximate the pharyngeal orifice of the eustachian tube 15 on the same side of the patients midline as the nostril engaged. From a mechanical standpoint, depressing the distal end of the canister at the open (superior) terminus of the administration housing with the device so oriented results in a release of compound through the collimation nozzle 49 (as discussed above). The compound released forms a well collimated stream which is directed towards the pharyngeal opening of the eustachian tube with great accuracy.

FIG. 12 illustrates the proper placement of the preferred embodiment of the present invention for correct operation. As shown in FIG. 12, the contoured distal portion 75 of the canister containment section alignment tab 73 is positioned against the bridge 17 of the nose. At the same time, the distal terminus 92 of the delivery nozzle section alignment tab 89 is placed so that the contoured portion 90 thereof is positioned against the patient in the vicinity of the philantrum 21. The administration device is also positioned so that the front wall of the housing is parallel to the facial plane of the patient. A patient's face may be described as having a facial plane with an X axis running medially, from the left to right side of the face, a "Y" axis running from the top to the bottom—superiorly/inferiorly—and a "Z" axis running directly into to the facial plane anteriorly/posteriorly from the front of the face to the back of the patient's head, The device of the present invention and the collimated stream provided thereby, is directed in alignment with both the "Z" axis—directly into the facial plane with no cant to the left or right—and with the midline of the device in alignment with the "Y" axis, devoid of any rotation. This orientation places the midline alignment line of the housing 95 in a parallel relation with the midline of the patients face and the front surface of the housing in parallel alignment with the patient's facial plane. The midline reference line 58 formed or printed upon the back surface of the housing section may be utilized in order to confirm proper positioning and also to correct any deviations which may occur.

Actuation of the canister, while the administration housing is positioned in this manner by depressing the distal end 71 of the canister the valve stem is biased against and depressed inwards by the housing docking port causing a release of compound through the collimation nozzle 49. The collimated stream of compound released from the distal opening of the collimation nozzle forms a well collimated stream 203 which is parallel to an nasal/tragus reference line 27, discussed above, in regard to elevation—running from the nostril to the tragus on the side of the face depicted. The nasal/tragus elevation alignment line necessary deviates laterally from the midline of the patients face as the line approaches the tragus as the tragus is located well lateral to the nostril. The device of the present invention is oriented so that the collimation nozzle is directed perpendicular to the facial plane and parallel to the midline of the patients face so as to avoid lateral deviation of the stream and to cause the stream to be directed, without medial or lateral deviation, directly back toward the pharyngeal opening of the eustachian tube. To be certain that the administration is properly aligned with the nostril to tragus line, a highly visible elevation alignment arrow 95 formed upon or within or upon the side walls of the delivery section of the housing provides a means of confirming proper placement of the device. It is highly advantageous to increase the visibility of this line/arrow by use of a contrasting color relative to the remainder of the administration housing.

Figure 14:
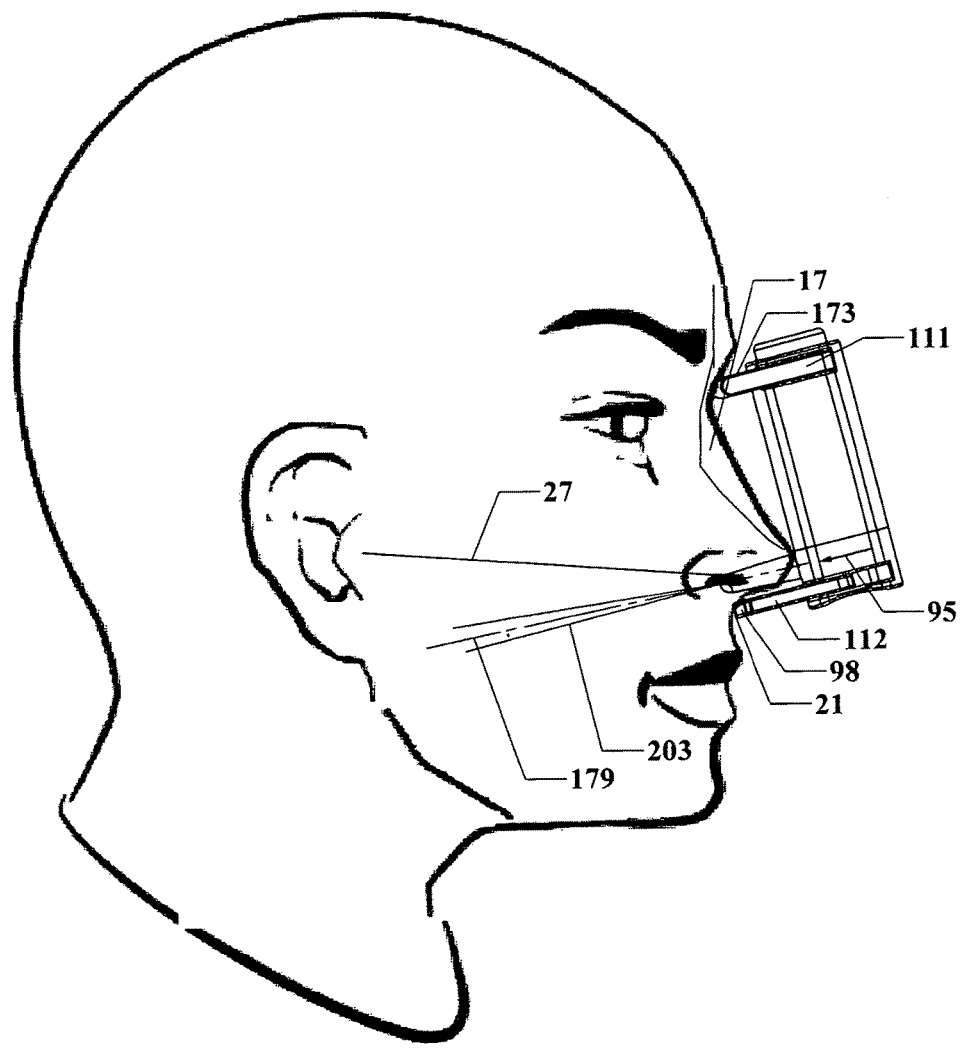
FIG. 14 illustrates a drawing of a person with the first alternate preferred embodiment of the present invention having a sliding canister containment section tab placed in a suboptimal operational position.
Figure 15:
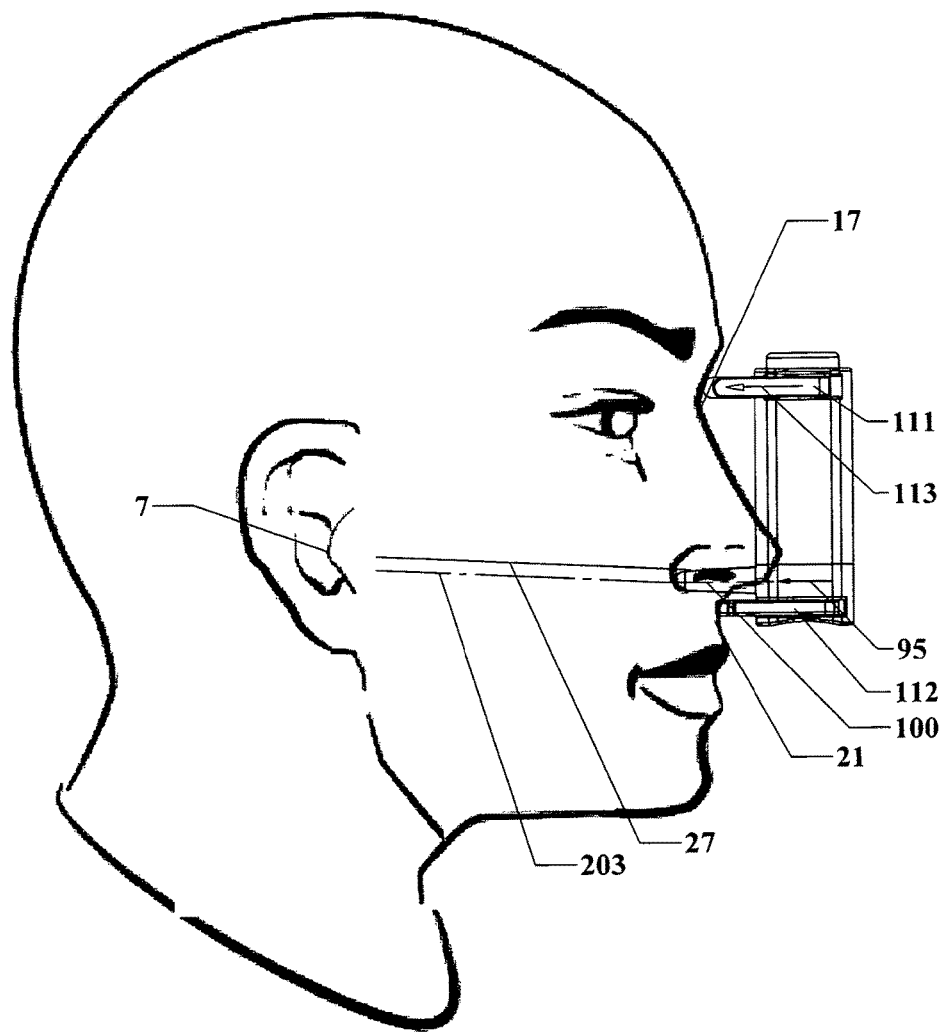
FIG. 15 illustrates a drawing illustrating the preferred embodiment of the present invention having a sliding canister containment section tab placed in an optimal operational position.
Figure 16:
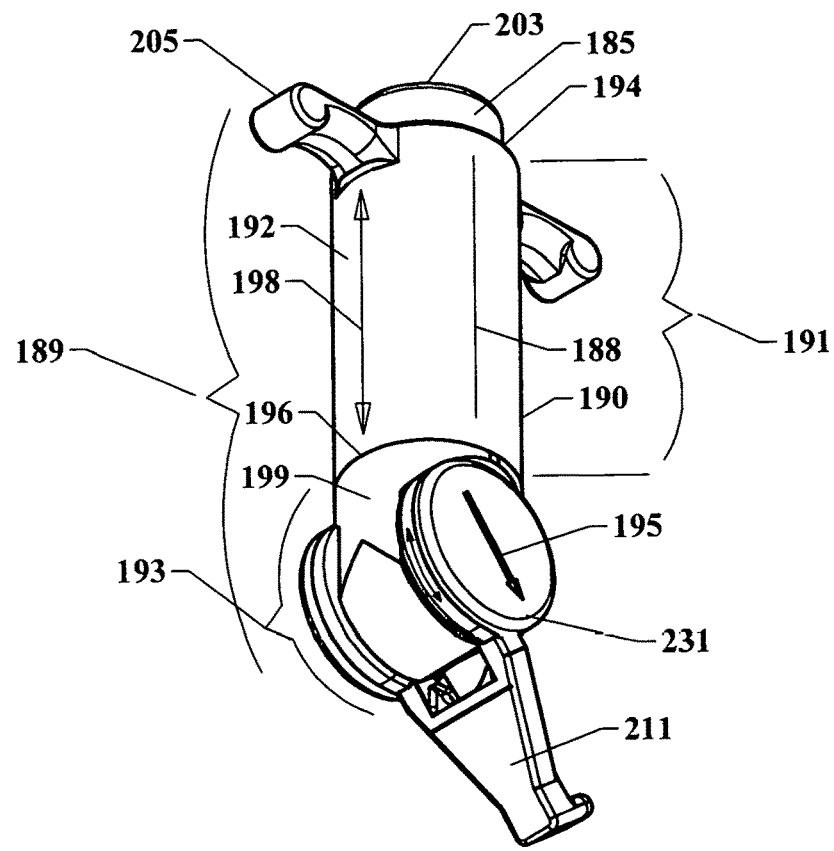
FIG. 16 is a rear isomeric view of the second alternate embodiment of the present invention.
Figure 17:
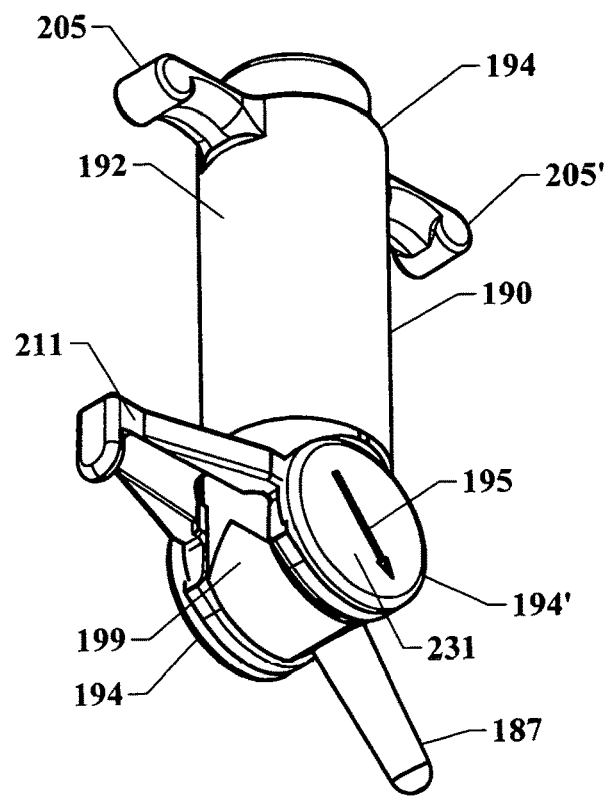
FIG. 17 illustrates the embodiment shown in FIG. 16 with the nozzle cover rotated to expose the delivery nozzle.
Figure 18:
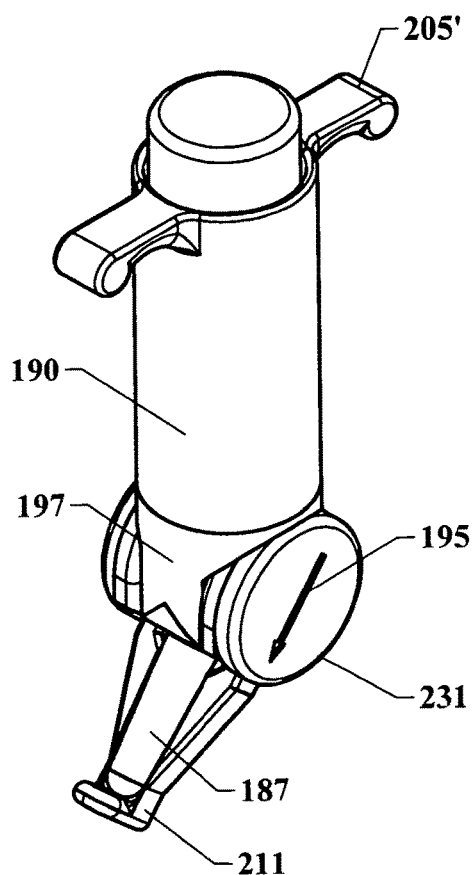
FIG. 18 is a front isomeric view of the second alternate embodiment of the present invention

FIGS. 14 and 15, illustrate the use of a preferred embodiment of the nasal administration device of the present invention configured with a slideable canister section alignment tab 111 and slideable delivery nozzle alignment tab 112. The present invention contemplates first alternate embodiments with a fixed delivery nozzle tab and a slideable canister section alignment tab, as well as embodiments wherein either or both alignment tabs are adjustable in regard to extension and retraction and/or movement along the longitudinal axis of the housing. In FIG. 14, the contoured distal portions 173 of the slideable tab 111 is positioned against the root section 17 of the nose with the tab in a middle (or neutral position). The neutral or as it may also be referred to as "halfway position" of the slideable canister tab is that position wherein it is extended away from the canister section one half the distance it is capable of extending at a full extension position. Put another way, the neutral or halfway position of the canister section alignment tab position is that position located halfway between the tabs fully extended and fully retracted positions. In this position, the tab extends from the canister containment section to the same degree and distance as the non-slideable (or, as they may also be equally referred to) "fixed alignment tabs" of the present invention.

At the same time that the canister section alignment tab is placed against the root portion of the nose, the distal terminus of the delivery nozzle section alignment tab 112 is placed so that the contoured portion 90 thereof is positioned against the patient in the vicinity of the philantrum 21, and more advantageously, upon the philtral column on the same side of the patient's face as the nostril entered. The adjustable delivery nozzle alignment tab is also in its neutral, halfway position which is the same position as a fixed version of the tab would provide.

The facial profile of the patient depicted in FIG. 14 includes a somewhat diminished mid-face contour so that the root portion and bridge of the patient's nose is positioned in relatively posterior position. Due to this profile, placement of contoured portion of the canister alignment tab against the root portion of the nose with the slideable canister alignment tab 111 in a neutral position, or, in embodiments without a slideable canister containment section tab, with the fixed canister tab against the 90 portion of the nose 17, results in suboptimal delivery of the collimated spray. More specifically, in such instances, and, as illustrated specifically in FIG. 14, the collimated stream 203 would be directed below the elevational level of the nasal/tragus elevation alignment line 27 and, consequently, cause the stream to be directed along line 179 below the eustachian tube pharyngeal orifice. More specifically, and, as illustrated in FIG. 14, actuation of the canister, while the administration housing is positioned in this manner, depressing the distal end 71 of the canister causes the valve stem of the canister to be biased against and depressed inwards by the housing docking port causing a release of compound through the collimation nozzle 49. The stream of compound released from the distal opening of the collimation nozzle forms a well collimated stream 203 which follows a path running below and inferior to the elevation of the nasal/tragus elevation alignment line 27, discussed above. The misalignment of the stream is immediately apparent by viewing alignment arrow 95. The alignment arrow is clearly pointed to an area below the tragus which provides a clear and unmistakable indication the device is being utilized in a suboptimal manner.

In embodiments of the present invention having only fixed alignment tabs (non-slideable), this misalignment can be corrected by attempting to move the device out of contact and away from the nose tilting the superior portion of the administrative housing in a direction away from the root portion of the nose so that the alignment arrow points towards the tragus. However, such alignment is somewhat unstable as only the delivery section tab remains in stable contact with the patient's face. Also, in regards to self-administration, such a situation ordinarily requires the use of a mirror or for a second person to align and administer and is also less stable in that there is no stabilizing contact between the alignment tab and the root portion of the nose.

In embodiments of the present invention having an adjustable canister alignment tab, the above-described suboptimal position can be overcome. More specifically, the canister alignment tab can be adjusted (extended outward 113) so that the alignment arrow formed upon the side walls of the delivery nozzle section points towards the tragus on the same side of the patient's face as the nostril entered. Since the slideable tab is configured so as to maintain its adjusted position once set, and to provide significant resistance against unintentional inward and outward movement. Once the slideable tab is so positioned, the administration device may be used repeatedly with no further need of tab adjustments with accurate targeting of the pharyngeal orifice of the eustachian tube. In embodiments of the present invention incorporating an adjustable delivery nozzle alignment tab, as illustrated in FIGS. 14 and 15, this tab may be retracted in order to provide further means of correcting the elevation of the nozzle and collimated nozzle stream to conform to properly target the pharyngeal orifice of the eustachian tube. Proper alignment can be attained by reference to the delivery nozzle section alignment arrow (and alignment of same with the tragus of the ear after insertion of the nozzle into the patient's nostril while the midline alignment line of the device is parallel to the midline of the patients face.

In regard to an excessively protrusive mid-face contour, the adjustable canister containment alignment tab is retracted to achieve proper alignment and, if the embodiment utilized includes an adjustable delivery section tab, that tab can also be extended to ameliorate the misalignment.

FIG. 15 illustrates the same side facial profile of the patient as illustrated in FIG. 14. However, in FIG. 15, the slideable canister containment section tab 111 is placed in a further extended position. The contoured distal portion of the slideable tab 111 is positioned against the bridge of the nose 17 with the tab in an extended position—. The proper degree of extension is determined by confirming that the alignment located on the side walls of the delivery nozzle section points to the patients tragus 7 when the contoured portions of both the canister containment and delivery nozzle tabs are in place against the nasion and philtrum of the patient (respectively). As shown in FIG. 15, with the adjustable canister alignment tab properly adjusted, the elevation alignment arrow points to the tragus and the collimated stream 203 emanating from the collimation nozzle 49. Such improved alignment may be achieved by extending an adjustable canister containment section tab, retracting an adjustable delivery nozzle section tab, or a combination thereof. In instances wherein there are other facial abnormalities such as, for example, an extremely prominent mid facial profile, as well as other facial variations, adjustment of the adjustable tabs with confirmation of proper positioning utilizing the delivery nozzle alignment arrow and midline alignment line provides effective eustachian tube targeting.

In a second alternate embodiment of the present invention, a nasal administration device which is especially configured and adapted for the delivery of medicaments through the nostril to the pharyngeal orifice of the eustachian tube of an infant. However, the second alternate embodiment may also b applicable to some adolescent and adult patients due to compliance, access and other clinical factors. FIGS. 16-19 illustrate the alternate embodiment of the administration device of the present invention. As in regard to the embodiments discussed above, the alternate embodiment of the present invention is especially designed, configured and adapted for the accurate and focused nasal administration of compositions to the pharyngeal orifice of the eustachian tube. The alternate embodiment of the present invention comprises a collimation nozzle 187 and an administration housing 189.

The canisters utilized with the second alternate preferred embodiment, including pressurized canister bottles with and without metered dose valves as well as canister bottles utilizing a mechanical pump system are well known to the art and as described above. The delivery nozzle utilized in the second alternate embodiment demonstrates the same regular, uniform and consistent diameter as disclosed above an is selected for preferred bore diameters for specific compositions as also discussed above in regard, for example, to administration of the mixture of lipid crystals discussed in great detail, above. However, the administration housing 189 utilized in the alternate embodiment is unique in its design and configuration which are required to be so in order to properly and most efficiently deliver medications in an infant or, for example, in less than compliant/accessible patients.

Due to the relatively diminutive size of an infant's head and face and, more importantly, the relative difference in facial profile between an infant and pediatric or adult profiles, it is highly advantageous to provide an administration housing that allows rapid and uncomplicated targeted delivery with a minimum of required steps. For this reason, the alternate embodiment of the present invention incorporates an administration housing comprised of a canister containment section 191 and a delivery nozzle section 193 devoid of the alignment tabs discussed above, but inclusive of an elevation alignment line/arrow 195 that is formed upon or within the side surfaces of the delivery nozzle section in alignment with the longitudinal axis of the collimation nozzle and the stream of medicine that is projected therefrom. The elevation alignment line/arrow enables a user to rapidly and correctly orient the device for proper direction of a medication stream towards the pharyngeal opening of the eustachian tube.

The canister containment section 191 of the housing is a simple, hollow tube, having a longitudinal axis 188, especially shaped and configured to contain and securely retain a canister 185 containing compound(s), mixtures and medicaments intended for application to the eustachian tube. As mentioned above, the canister utilized may be a pressurized canister utilizing a propellant—in liquid or gas form—or such canister may simply incorporate a mechanical pump for directing such compound(s), mixtures and/or medicaments through the conduits of the second alternate embodiment. Such canisters included metered dose canisters utilizing liquid, gas or a combination of same as a propellant. The canister containment section includes a front portion 190, a rear portion 192, a superior terminus 194 and an inferior terminus 196. The superior terminus 194 is open which enables passage therethrough of a canister bottle. The inferior terminus 196 of the canister containment section is especially shaped and configured to mate with and engage the delivery nozzle section 193 discussed below. The containment canister section may advantageously demonstrate a length slightly less than the length of the canister bottle so as to enable a small portion of the distal end 203 of the canister to extend beyond the canister containment section so as to allow access to depress the bottle for actuation of the metering valve and release of compound(s), mixture(s) and/or medication from the device. The canister containment section also includes two finger rests 205/205' extending from the front and back portion of the section adjacent to the proximal terminus thereof located approximately opposite one another (in a 180 degree relation). The finger rests provide, as discussed below, a means of holding and quickly manipulating the position of the device during use as well as finger holds to bias against when depressing the distal end of the canister bottle with, for example, an additional finger during operation of the device. Centered upon the rear portion of the canister containment section 191 of the housing a midline alignment mark 198 is provided running parallel to the longitudinal axis 188 of the canister containment section. When utilizing the nasal administration device of the present invention, the device is oriented so that the midline alignment mark faces away from the infant's face, as shown in the figures, and parallel to the midline of the face, so that the collimation nozzle is oriented directly into the plane of the infant's face.

The delivery nozzle section 193 of the administration housing defines a short hollow cylinder having two side surfaces 194/194', a front surface 197 and a back surface 199. The delivery nozzle section of the administration housing also demonstrates a superior terminus 218 especially shaped and configured to matingly engage the inferior terminus of the canister containment section. The delivery nozzle section further demonstrates a rounded closed inferior terminus 219 and a central bore especially configured and adapted to contain a docking port 223 therein (as described, below). In certain examples of the second alternate embodiment of the present invention, a rotating delivery nozzle cover, as described below, is provided. In such embodiments, both side surfaces of the delivery nozzle section are especially shaped and configured to include rotation posts 212/212' which matingly engage nozzle cover rotation rings 210/210'. The rotation rings, as discussed below, enable the nozzle cover 211 of such embodiments incorporating same to rotate so as to cover and uncover the collimation nozzle.

The delivery nozzle section of the second alternate embodiment includes a nozzle port 209 located on the front surface thereof adjacent to the inferior terminus. The nozzle port is especially configured and adapted for secure engagement of the collimation nozzle 187 of the present invention. The nozzle port is positioned upon the barrel shaped portion of the nozzle section so that it arises from the front surface of the device and opposite the rear surface midline alignment mark discussed above. This configuration enables a user who positions the device so that the midline alignment mark appears centered on the back surface of the device when positioned in a patient's nostril—and parallel to the midline of the patient's face, assures that collimated stream administered by the device is applied directly into the patients nose, nasal antrum and nasopharynx without lateral or medial deviation. Such alignment, along with the elevational alignment of the device alignment arrow/line discussed below with the tragus of the patient's ear, provides excellent targeting of the pharyngeal opening of the eustachian tube. The nozzle port 209 may advantageously be positioned so as to depend downward at an approximately 135 degree angle as shown in the figures. Such angulation facilitates the ease of aligning the collimation nozzle, via the elevation alignment line/arrow formed within or upon the side surface of the delivery nozzle section, so that it is directed towards the patient's tragus after insertion of the nozzle into the patient's nose.

As mentioned above, the second alternate embodiment of the present invention may include a rotating nozzle cover assembly 211 depending from and rotating about the rotation posts 212'/212 which depend from the side surfaces of the delivery nozzle section. The rotating nozzle cover provides covering and uncovering of a nozzle cover for protection against contamination.

A housing junction is located between the superior terminus of the delivery nozzle section 218 and the inferior terminus of the canister containment section 196. Within the central bore of the delivery nozzle section, the delivery nozzle section includes a docking port 223 especially designed, shaped and configured to securely mate and engage the distal portion 49 of a canister, such as, for example, a metered dose canister 185 as well as the valve stem 51 extending from the metering valve assembly therein. A conduit, 225 which includes an opening at either end thereof, is formed within the docking port and runs continuously from the docking port to and through the nozzle port 209. This conduit provides a continuous fluid pathway and communication between the central bore of the valve stem when docked at the docking port—and the bore of the collimation nozzle 187 affixed to the nozzle port—. An engagement sleeve may be advantageously utilized to join the administration nozzle with the canister containment nozzle.

Figure 19:
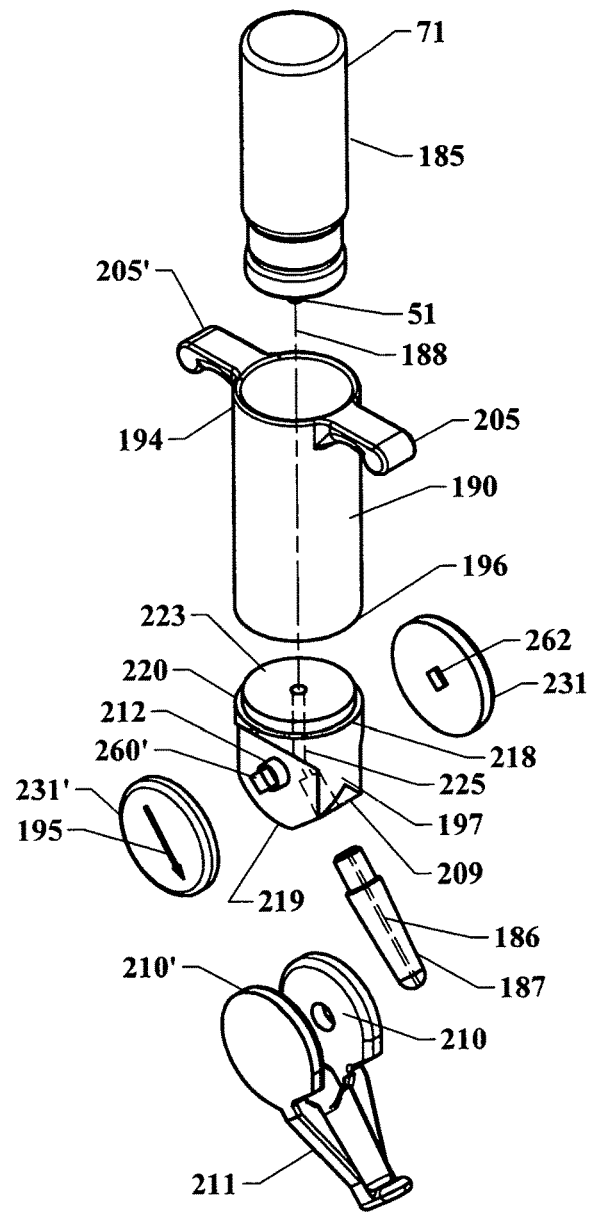
FIG. 19 is and exploded view of FIG. 18.

End caps 231 located lateral to the rotation rings 210/210' cover, but do not rotate with the nozzle cover. Although, as illustrated in FIG. 19, the end caps are mounted upon posts 212'/212 they are mounted upon a portion of said posts in a non-rotating manner. For example, as shown in FIG. 19, the end caps include a central mounting recess which is configured as a square recess 262/262' which enable the end caps to mount upon a square end portion 260/260' of rotation posts 212/212' In embodiments of the present invention utilizing rotating end caps, the elevation alignment line/arrows formed upon or within the side surfaces of the delivery nozzle section are advantageously positioned on such end caps in such a manner as to be in alignment with the collimation nozzle depending from the front surface of the second alternate embodiment of the present invention. Rotation of the rotation rings of the end cap assembly does not cause the alignment arrows/lines to rotate as such end caps are in a fixed position.

In those examples of the second alternate embodiment not incorporating such rotating end caps, the alignment arrow/line are formed upon or within the side surfaces of the delivery nozzle section in a like manner, parallel to and in alignment with the collimation nozzle. The elevation alignment lines/arrows are placed so as to be in alignment with the longitudinal axis of the collimation nozzle mounted upon the administration nozzle section as well as the collimated stream of any composition emanating therefrom. The term elevation alignment lines/arrows means that the indicators formed upon or within the end caps providing alignment reference may be formed of a simple straight line or a line with an arrowhead.

In practicing the method of the alternate embodiment of the present invention, a metered dose canister filled with the appropriate and desired medication is placed within the administration housing so as to securely engage the docking port. In alternate embodiments of the present invention incorporating a rotating nozzle cover assembly, the nozzle cover is rotated away from the distal terminus of the collimation nozzle prior to each use so as to expose same for use.

Thereafter, the housing is securely engaged and held by a user utilizing the finger rests. Thereafter, the collimation nozzle is positioned within an external nasal orifice of a patient to receive the medication provided by the device. Thereafter the device is manipulated and positioned by a user until the elevation alignment line/arrow is positioned so as to a align with an imaginary line running from the nasal orifice to the tragus of the ear of the patient on the same side of the patient's head as the nasal orifice engaged by the collimation nozzle. At the same time, the administration housing is aligned so that the midline alignment line 198 is aligned with the midline of the infant's face and oriented 180 degrees away from the child's facial plane. In such an alignment, the plane of the infant's face is considered to be oriented so that the midline of the face is equivalent to the "Y" axis while the "X" axis would be oriented running from the left to right side of the plane of the face. A "Z" axis would be running directly into the plane of the face at a 90 degree angle and intersection the "X" and "Y" axis at the their intersection . . . the origin. In properly positioning the second alternate embodiment, the midline alignment line on the back surface of the device is aligned to be parallel with the midline of the infant's face—which can also be referred to as the "Y" axis of the facial plane—. If the embodiment includes a delivery nozzle which depends from the front portion of the delivery nozzle section at a 135 degree relation, as shown in FIGS. 16 to 19, when the device is properly positioned with the elevation alignment arrow pointing to the tragus, the long axis of the delivery nozzle section and canister containment section (which run along the same axis) will diverge away from the infants facial plane along the "Z" axis. However, in properly positioning the second alternative embodiment, such divergence away from the nasal/tragus medial/lateral deviation is ignored as alignment, in that regard, would direct the collimated spray laterally, away from the eustachian tube orifice. As mentioned above in regard to a child's or adults face, an infant's face may be described as having an X axis running medially, from the left to right side of her face, a "Y" axis running superiorly/inferiorly, from the top to bottom of the face and a "Z" axis running directly into to the face (facial plane) anteriorly/posteriorly from the face to the back of the infant's head. The device of the second preferred embodiment is positioned so that the collimated stream provided thereby, is directed in alignment with the "Z" axis—directly into the facial plane—and with the "Y" axis. For this purpose, the administration device is positioned so that the midline alignment line of the device is in alignment with the midline of the face (the "Y" axis) and also positioned so that the collimation nozzle is oriented directly into the facial plane without medial or lateral deviation.

Once the device is so positioned, the user pushes upon so as to depress the metered dose container further into the housing and against the docking port so as to cause the metered dose actuator valve to release a dose of the medication contained within the container so as to flow through the bore of the docking port and through the collimation tube. Since the elevation alignment line/arrow is aligned with an imaginary line running from the nasal orifice to the tragus, and the collimated stream flowing from the device is aligned with said same pathway, the stream of medication dispensed from the device is accurately directed towards the pharyngeal orifice of the eustachian tube.

We claim:

1. A nasal administration device especially configured and adapted to deliver a composition to an eustachian tube lumen of a human patient via the pharyngeal orifice thereof, said device comprising an administration housing and a delivery nozzle wherein:
   the administration housing is configured to contain the composition to be delivered e therein and includes an alignment tab extending therefrom having a proximal and distal terminus, the proximal terminus of the tab depending from the administration housing and the distal terminus being especially shaped an configured to enable stable placement thereof upon the patient's nose at a bridge portion thereof; and
   the delivery nozzle being formed as a hollow tube and including a central bore with a longitudinal axis, a proximal and distal termini, both said termini including openings in fluid communication with said central bore, the central bore and said openings all demonstrating an equal, constant and continuous diameters, the distal terminus and distal portion of said nozzle being especially shaped and configured to facilitate placement thereof within a nostril of the patient and the proximal terminus of said nozzle being especially shaped and configured to enable mounting thereof upon the administration housing so as to provide fluid communication of the central bore and terminal openings of the nozzle with the composition contained within the administration housing, the diameter of the delivery nozzle being especially selected to further facilitate the nozzle forming and delivering a well focused collimated stream of compound upon activation of and resulting release of the composition from the device, wherein, when the delivery nozzle is placed within a patient's nostril while the alignment tab is positioned against the bridge portion of the patient's nose, the design, shape, dimensions, and position of said alignment tab stabilizes the device's position and causes the longitudinal axis of the central bore of the delivery nozzle to be aligned in such a manner so that, upon activation of the device, the collimated stream of compound emanating therefrom is directed towards the pharyngeal opening of the eustachian tube.

2. The device of claim 1 wherein the administration housing additionally includes an elevational alignment arrow positioned upon an outer surface of said housing in such a manner as to be in parallel alignment with the longitudinal axis of the delivery nozzle.

3. The nasal administration device of claim 1 wherein the administration housing comprises a canister containment section and a delivery nozzle section;
   the canister containment section having a front wall, rear wall, two side walls, an inferior terminus, a superior terminus and a central bore and a longitudinal axis, both termini having openings continuous with said central bore, the alignment tab being a cannister section alignment tab depending from and extending forward of said front wall of the canister section;
   the delivery nozzle section demonstrating a superior terminus, an inferior terminus, a front wall, a back wall, two side walls and a central bore, the central bore including a canister docking port especially configured and adapted for insertion and retention of a distal portion of a canister containing the composition to be delivered, the docking port also including a conduit formed therewithin especially configured to enable fluid communication with the composition contained within a canister docked therewithin upon activation of the canister, the delivery nozzle section also including a delivery nozzle port located upon the front wall thereof having a central bore therewithin, the delivery nozzle port being positioned upon the front wall of the delivery nozzle section in such a manner as to enable fluid communication between the central bore of the nozzle port and the conduit formed within the docking port;
   the proximal terminus of the delivery nozzle being especially shaped and configured to enable mounting thereof upon the delivery nozzle port in such a manner as to provide fluid communication between the central bore of the nozzle port and the delivery nozzle.

4. The nasal administration device of claim 3 wherein the side walls of the delivery nozzle section includes an elevation alignment arrow which is positioned and configured so as to be in parallel alignment with the longitudinal axis of the central bore of the delivery nozzle as well as the collimated stream of a composition emanating therefrom.

5. The nasal administration device of claim 4 wherein the canister containment section alignment tab is an adjustable tab which is especially designed, adapted and configured to extend forward away from the front wall of the device and retract back towards the front wall of the device.

6. The nasal administration device of claim 5 wherein the adjustable canister containment section alignment tab provides, in addition to extension and retraction adjustment, adjustment of proximal and distal position of the tab along the longitudinal axis of the canister containment section.

7. The nasal administration device of claim 4 further comprising a midline alignment line formed upon a midline of the rear wall of the canister containment housing in such a position as to be aligned with the longitudinal axis of the central bore of the canister containment section.

8. The nasal administration device of claim 3 further comprising a delivery nozzle section alignment tab having a proximal and a distal terminus, the proximal terminus depending from said delivery nozzle section and the distal terminus being especially shaped, contoured and configured for stable placement thereof in the region of a philtral column of a patient.

9. The nasal administration device of claim 8 wherein the side walls of the delivery nozzle section includes an elevation alignment arrow which is positioned and configured so as to be in parallel alignment with the longitudinal axis of the central bore of the delivery nozzle as well as the collimated stream of a composition emanating therefrom.

10. The nasal administration device of claim 9 wherein the canister containment section alignment tab is an adjustable tab which is especially designed, adapted and configured to extend forward away from the front wall of the device and retract back towards the front wall of the device.

11. The nasal administration device of claim 10 further comprising a midline alignment line formed upon a midline of the rear wall of the canister containment housing in such a position as to be aligned with the longitudinal axis of the central bore of the canister containment section.

12. The nasal administration device of claim 9 further comprising a midline alignment line formed upon a midline of the rear wall of the canister containment housing in such a position as to be aligned with the longitudinal axis of the central bore of the canister containment section.

13. A method of delivering a collimated stream of a composition to a eustachian tube lumen in a human patient utilizing a nasal administration device containing a composition to be delivered wherein the administration device includes an administration housing having a first alignment tab depending therefrom especially shaped and configured for stable placement upon a patient's nose, and a delivery nozzle especially designed and configured to direct said collimated stream to the pharyngeal orifice of the eustachian tube comprising:
  positioning the device so that the first alignment tab comes into stable contact with the bridge portion of the patient's nose;
  positioning the device so that the delivery nozzle enters and is placed within a nostril on one side of the patient's face; and thereafter
  activating the administration device so that the composition, contained within the administration housing, flows through the device, forms a collimated stream within the delivery nozzle and is directed thereby through the nostril entered and towards the pharyngeal orifice of the patient's eustachian tube.

14. The method of claim 13 wherein the administration housing further includes an elevation alignment arrow and wherein said method further comprises adjusting the position of the administration device so that the elevation alignment arrow points towards a tragus portion of the patient's ear on the same side of the patient's face as the nostril entered.

15. The method of claim 14 wherein the nasal a administration device additionally includes a midline alignment line formed upon the administration housing and wherein said method further comprises adjusting the position of the device so that the midline alignment line is in parallel alignment with a midline of the patient's face.

16. The method of claim 14 wherein the first alignment tab is an adjustable alignment tab which is retractable towards and extendable away from the administration housing and wherein the method further comprises adjusting the first alignment tab so that when it is in stable contact with the bridge portion of the patient's nose and the delivery nozzle is placed within the patient's nostril, the elevation alignment arrow points towards a tragus portion of the patient's ear.

17. The method of claim 16 wherein the nasal administration device includes a second alignment tab and wherein said method further comprises positioning the device so that the second alignment tab comes into stable contact with the patient's face just below the nostril in which the administration nozzle is placed and enters.

18. The method of claim 17 wherein the the nasal administration device also includes a midline alignment line and wherein said method further comprises adjusting the position of the administration device so that the midline alignment line is in parallel alignment with a midline of the patient's face.

19. The method of claim 18 wherein the second alignment tab is an adjustable alignment tab which is retractable towards and extendable away from the administration housing and wherein the method further comprises adjusting the position of the administration device by adjusting the second alignment tab so that when the first alignment tab is positioned against the bridge portion of the patient's nose and the second adjustment tab is placed in contact with the patient's face just below the nostril in which the administration nozzle is placed, the elevation alignment arrow points towards a tragus portion of the patient's ear.

20. The method of claim 19 wherein the first alignment tab is adjustable in relative to extension and retraction as well as proximally and distally along a longitudinal axis of the administration housing and wherein the method further comprises adjusting the position of the first alignment tab along the longitudinal axis of the administration device so that when the first alignment tab is positioned against a bridge portion of the patient's nose, the delivery nozzle is aligned with the nostril entered and the second adjustment tab is in stable contact with the patient's face just below the nostril in which the administration nozzle is placed.

21. The method of claim 13 wherein the nasal administration device includes a second alignment tab and wherein said method further comprises positioning the device so that the second alignment tab comes into stable contact with the patient's face just below the nostril in which the administration nozzle enters and is placed.

22. The method of claim 21 wherein the nasal administration device additionally includes an elevation alignment arrow and wherein said method further comprises adjusting the position of the administration device so that the elevation alignment arrow points towards a tragus portion of the patient's ear on the same side of the patient's face as the nostril entered.

23. The method of claim 22 wherein the nasal administration device additionally includes a midline alignment line and wherein said method further comprises adjusting the position of the administration device so that the midline alignment line is in parallel alignment with a midline of the patient's face.

24. A nasal administration device especially configured and adapted for targeted delivery of a composition to an eustachian tube lumen of an infant human patient via the nasopharyngeal orifice of the eustachian tube, said device comprising an administration housing and a delivery nozzle wherein:
  the administration housing is comprised of a canister containment section and a delivery nozzle section;

the canister containment section is shaped and configured as a hollow tube having a central bore and longitudinal axis and is especially shaped and configured to contain and securely retain a canister bottle, the canister containment section demonstrating a front portion, rear portion, two side portions, a superior terminus and an inferior terminus, the superior terminus including an opening which enables passage therethrough of the canister bottle and the inferior terminus of the canister containment section being especially shaped and configured to mate with and securely engage a superior terminus of the delivery nozzle section, the canister containment section also including two finger rests extending from outer surfaces of the front and rear portions thereof, adjacent to the superior terminus of the canister containment section, the finger rests providing a means to hold and manipulate the position and orientation of the device during use as well as providing finger holds utilized to stabilize the device when a user presses against, so as to activate, a canister bottle during operation of the device;

the delivery nozzle section is formed as a short hollow cylinder having two side surfaces, a front surface, a back surface, an open superior terminus and a closed rounded inferior terminus, the superior terminus being especially shaped and configured to matingly engage the inferior terminus of the canister containment section, the delivery nozzle section especially configured and adapted to contain a docking port therein, the delivery nozzle section further including a nozzle port located on the front surface adjacent to the inferior terminus thereof, the nozzle port being especially configured and adapted for secure engagement of the delivery nozzle, said delivery nozzle including a central bore having a longitudinal axis, the side surfaces of the delivery nozzle section also including elevation alignment lines which are placed, positioned and oriented so as to be in alignment with the longitudinal axis of the delivery nozzle as well as a collimated stream of a composition emanating therefrom during activation of said device;

the docking port, located within the delivery nozzle section is especially designed, shaped and configured to securely mate with and engage a distal portion of a canister bottle contained within the administration housing, the docking port including therewithin a conduit which includes an opening at either end thereof and running continuously from the docking port to and through the nozzle port, said conduit providing a continuous fluid pathway and fluid communication between a composition contained within the canister when docked at the docking port—and the bore of the delivery nozzle affixed to the nozzle port;

the delivery nozzle being formed as a hollow tube and including said central bore, said longitudinal axis, a proximal and distal termini, both said termini including openings in fluid communication with said central bore and said openings and central bore of the nozzle, all demonstrating an equal, constant and continuous diameter, the distal terminus and distal portion of said nozzle being especially shaped and configured to facilitate placement thereof within a nostril of the infant and the proximal terminus of said nozzle being especially shaped and configured to enable mounting thereof upon the nozzle port so as to provide fluid communication of the central bore and terminal openings of the nozzle with the composition contained within the canister, the diameter of the delivery nozzle being especially selected to facilitate the nozzle forming and delivering a well focused, collimated stream of compound upon activation of and resulting release of the composition from the device, wherein, when the delivery nozzle is placed within an infant's nostril and the device is positioned so that the longitudinal axis of the administration housing is aligned with a midline of the infant's face while the elevation line is oriented towards a tragus of the infant's nose, activation of the device directs a collimated stream of compound emanating therefrom towards the nasopharyngeal opening of the infant's eustachian tube.

25. The nasal administration device of claim 24 wherein the the rear portion of canister containment section includes a midline alignment mark running parallel to the longitudinal axis thereof and the nozzle port is located on the front surface of the delivery nozzle section opposite said midline alignment mark wherein, when the delivery nozzle is placed within an infant's nostril and the device is positioned so that the midline alignment mark is aligned with the midline of the infant's face while the elevation line is oriented towards a tragus of the infant's ear, activation of the device directs a collimated stream of compound emanating therefrom towards the nasopharyngeal opening of the infant's eustachian tube.

26. The nasal administration device of claim 24 wherein the canister is a metered dose canister bottle.

27. The nasal administration device of claim 24 wherein the canister bottle is a pump actuated canister bottle.

28. The nasal administration device of claim 24 wherein the device further comprises a rotating delivery nozzle cover which is rotatably mounted, by means of two rotation rings extending therefrom, upon rotation posts that extend from both side surfaces of the delivery nozzle section.

* * * * *